(12) United States Patent
Dreano et al.

(10) Patent No.: US 7,951,359 B2
(45) Date of Patent: May 31, 2011

(54) COMPOSITIONS AND METHODS FOR THERAPY OR PREVENTION OF CHEMOTHERAPY-INDUCED NEUROPATHY

(75) Inventors: Michel Dreano, Weston, MA (US); Pierre-Alain Vitte, Cranves Sales (FR)

(73) Assignee: Merck Serono SA, Coinsins, Vaud (CH)

( * ) Notice: Subject to any disclaimer, the term of this patent is extended or adjusted under 35 U.S.C. 154(b) by 518 days.

(21) Appl. No.: 11/587,937

(22) PCT Filed: Apr. 28, 2005

(86) PCT No.: PCT/IL2005/000444
§ 371 (c)(1), (2), (4) Date: Jan. 30, 2008

(87) PCT Pub. No.: WO2005/105135
PCT Pub. Date: Nov. 10, 2005

(65) Prior Publication Data
US 2008/0193409 A1    Aug. 14, 2008

(30) Foreign Application Priority Data
Apr. 29, 2004    (IL) .......................................... 161673

(51) Int. Cl.
*A61K 38/20* (2006.01)
(52) U.S. Cl. ...................................... 424/85.2; 514/21.2
(58) Field of Classification Search ........................ None
See application file for complete search history.

(56) References Cited

U.S. PATENT DOCUMENTS
2008/0107621 A1    5/2008 Dreano et al.

FOREIGN PATENT DOCUMENTS
WO    WO 03/033015 A    *    4/2003

OTHER PUBLICATIONS

McWhinney et al., Platinum neurotoxicity pharmacogenetics, Mol Cancer Ther. 8(1):10-6 (2009).
Quasthoff and Hartung, Chemotherapy-induced peripheral neuropathy, J. Neurol. 249:9-17 (2002).
Kaley and DeAngelis, Therapy of chemotherapy-induced peripheral neuropathy, British Journal of Haematology, 145:3-14 (2009).
Scripture et al., Peripheral neuropathy induced by paclitaxel: recent insights and future perspectives, Curr Neuropharmacol. 4(2):165-72 (2006).
Sioka and Kyritsis. Central and peripheral nervous system toxicity of common chemotherapeutic agents, Cancer Chemother Pharmacol 63:761-767 (2009).
I. G. Obrosova, Diabetes and the periopheral nerve, Biochim. Biophys. Acta 1792:931-940 (2009).

* cited by examiner

*Primary Examiner* — Prema Mertz
(74) *Attorney, Agent, or Firm* — Browdy and Neimark, PLLC

(57) ABSTRACT

The present invention relates to the use of IL-6 in compositions and methods for therapy or prevention of chemotherapy-induced neuropathy (CIPN). More specifically, the invention relates to the use of a low dose of IL-6 for the treatment and/or prevention CIPN.

10 Claims, 34 Drawing Sheets

Figure 30 (continuation)
E
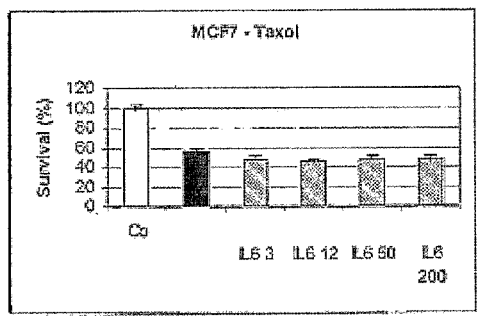
F
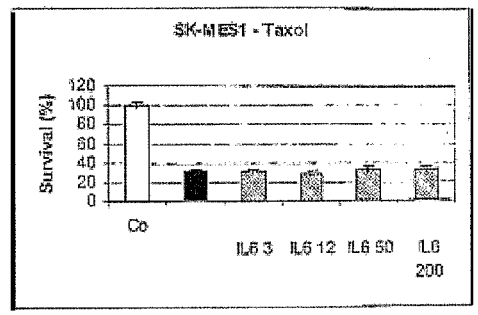
G
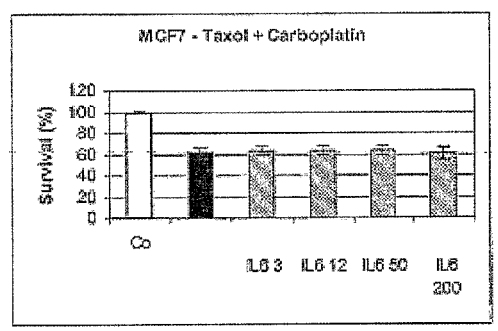
H
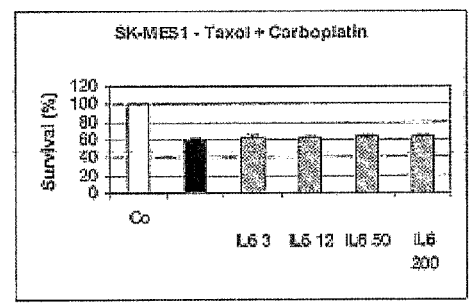
I
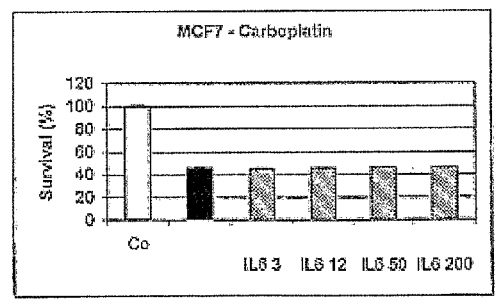
J
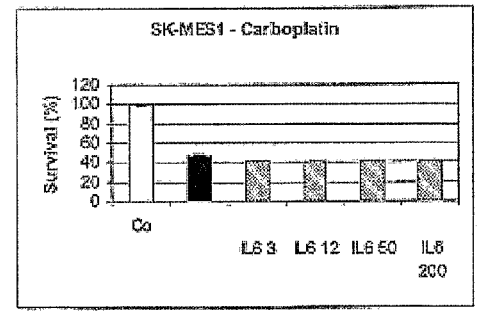

COMPOSITIONS AND METHODS FOR THERAPY OR PREVENTION OF CHEMOTHERAPY-INDUCED NEUROPATHY

FIELD OF THE INVENTION

The present invention relates to the use of IL-6 in chemotherapy-induced neuropathy (CIPN). More specifically, the invention relates to the use of a low dose of IL-6 for the treatment and/or prevention of chemotherapy-induced neuropathy.

BACKGROUND OF THE INVENTION

Peripheral neuropathy is a complex of disorders of the peripheral nervous system resulting from damage to the nerve or to the myelin sheath. The damage is long lasting, usually outlasting the injury that initiates it.

Chemotherapy-induced peripheral neuropathy (CIPN) is a common and potential disabling side effect of many cytotoxic drugs. Chemotherapy-induced neuropathy is related to cumulative dose or dose-intensities (Verstappen et al. 2003 Drugs 63:1549-63).

Currently, CIPN is alleviated only by dose reduction, which may compromise the efficacy of the chemotherapy treatment. Patients who already have neuropathic symptoms due to diabetes mellitus, hereditary neuropathies or early treatment with neurotoxic chemotherapy are thought to be more vulnerable for the development of CIPN.

The vinca-alkaloids (e.g. vincristine and vinblastine), platinum-based compounds (e.g. cisplatin) and taxanes (paclitaxel and docetaxel) are amongst the most important drugs inducing peripheral neurotoxicity (Visovsky C. Cancer Invest. 2003 June; 21(3): 439-51), Quasthoff S, Hartung H P J. Neurol. 2002 January; 249(1): 9-17. Review). These drugs are widely used for treatment of various malignancies such as ovarian, breast cancer, and haematological cancers (Verstappen et al. 2003 Drugs 63(15): 1549).

Vincristine-driven neuropathy is mainly characterized by motor and sensory insufficiency (mixed type of neuropathy). Whilst the underlying mechanism is not fully understood as yet, it has been described to involve an alteration of anterograde axonal transport, ultimately leading to axonal degeneration. Up to now, treatment of vincristine-driven neuropathy is only palliative, as no efficient therapy has been developed so far.

Cis-dichlorodiamine platinum (cisplatin) is the drug of choice for treatment of germ cell cancers. It is also used adjunctively for other solid tumors but the total dose that can be administered is limited by serious adverse effects including renal toxicity and peripheral neurotoxicity. The incidence of nephropathy, which was dose limiting, has been significantly reduced by chloride diuresis. Problems of peripheral neuropathy appear soon after the drug is introduced. The neuropathy is dose limiting and closely related to total cumulative drug dose. Significant peripheral neurotoxicity is apparent in the majority of adult patients who receive >400-500 mg/m$^2$ of cisplatin. The neuropathy is predominantly sensory with initial complaints of paresthesiae (abnormal sensation as burning, prickling, formication) in the distal extremities, which may progress to severe sensory ataxia. Neuropathological studies have shown loss of large myelinated fibers and evidence of axonal degeneration. The neuropathy may continue to progress for several months after cessation of cisplatin and symptoms may develop 3-8 wk after the last dose of chemotherapy (Thompson et al., (1984) Cancer. 54(7): 1269-75). Studies of tissue platinum assays, monitoring the tissues in which platinum accumulates, revealed the highest platinum concentration in tumor tissue, but similarly high concentrations were found in peripheral nervous tissue. This compared with much lower concentrations in brain. Electrophysiological studies in cancer patients treated with cisplatin confirm that large diameter sensory axons are involved.

Taxol is an effective chemotherapeutic agent extensively used in the treatment of solid tumors such as malignant melanoma and ovarian carcinoma. Nevertheless, peripheral neuropathy caused by taxol is increasingly becoming a dose-limiting problem in cancer treatment (Rowinsky E. K., Chaudhry V., Cornblath D. R, Donehower R. C. Neurotoxicity of taxol (1993). Monogr. Natl. Cancer Inst. 107-115.). Taxol is a plant alkaloid that suppresses microtubule dynamics through binding to tubulin subunits, causing mitotic arrest in dividing cells (Derry W. B, Wilson L., Jordan M. A. Sub-stoichiometric binding of taxol suppresses microtubule dynamics (1995) Biochemistry 34: 2203-2211.), and axonal degeneration in peripheral nerve due to interference with axonal transport (Rowinsky et al., 1993). The resulting neuropathy predominantly affects small sensory fibers, but at higher doses motor and large sensory fiber dysfunction occur (Freilich R. I., Balmaceda C., Seidman A. D., Rubin M., DeAngelis L. M. Motor neuropathy due to docetaxel and paclitaxel (1996). Nutr. Rev. 47: 115-118).

In general, treatment of peripheral neuropathy is symptomatic and has no beneficial effect underlying damage to the nerves (Peltier A C, Russell J W. Recent advances in drug-induced neuropathies. Curr Opin Neurol. 2002 October; 15(5): 633-8). For example, pyridoxine (vitamin B6) is used as a method of nutritional support following peripheral nerve damage, antioxidants (e.g. gamma-linoleic acid, alphalipoic acid, and PKC inhibitors and aldose reductase inhibitors) are used to eliminate toxins which may contribute to peripheral neuropathy, anticonvulsant are used to suppress the pain symptoms. Attempts to prevent vincristine-neuropathy using putative neuroprotective agents such as vitamin B1, vitamin B12, glutamate (Boyle et al. J Pharmacol Exp Ther. 1996 October; 279(1): 410-5.), isoaxonine (Le Quesne et al., J Neurol Neurosurg Psychiatry. 1985 September; 48(9): 933-5.), gangliosides or nerve growth factor (Hayakawa et al., Life Sci. 1994; 55(7): 519-25. 4; Lewis et al. Exp Neurol. 1993 November; 124(1): 73-88.) showed limited success.

In particular, common approaches for treatment of chemotherapy-induced neuropathy include the following: dose and duration-limitation of chemotherapeutic agents, and use of nerve growth factor (NGF) and Glutamine (Peltier A C, Russell J W. Recent advances in drug-induced neuropathies. Curr Opin Neurol. 2002 October; 15(5): 633-8).

4-methylcatechol (4-MC) is a catechol derivative having beneficial effects in sciatic nerve regeneration and in two experimental models of diabetic neuropathy [Hanaokoa and Ohi J. Neurolog. 1994 122, 28-32, and Saita et al. J. Pharmacol. Exp. Ther. 1996, 276, 231-237]. Catechol derivatives such as 4-methylcatechol (4-MC), stimulate the production of nerve growth factor (NGF) from cultured astrocytes in vitro and in vivo [Takeuchi et al. FEBS Lett 1990, 261, 63-66] and induce brain-derived neurotrophic factor (BDNF) in rat brain [Nitta et al J. Pharmacol. Exp. Ther. 1999, 291, 1276-83]. However, the therapeutic utility of catechols is not clear, since they are reactive chemicals and may produce numerous side effects or drug-drug interaction at therapeutic concentrations (Schweigert et al. 2001 Environmental Microbiology Volume 3 Issue 2 Page 81).

IL-6 acts not only as a pro—but also as an anti inflammatory cytokine (Jones et al. FASEB J. 2001 January; 15(1):

43-58. Review). The functional properties of IL-6 are extremely varied and this is reflected by the terminology originally used to describe this cytokine (Horst Ibelgaufts' COPE: Cytokines Online Pathfinder Encyclopaedia).

Two proteins bind IL-6, IL-6 receptor (IL-6R) and gp130 (reviewed by Hirano et al Stem Cells. 1994 May; 12(3): 262-77. Review). Soluble forms of IL-6R (sIL-6R), corresponding to the extracellular domain of gp80, are natural products of the human body found as glycoproteins in blood and in urine (Novick et al, J. Chromatogr. 1990 27; 510:331-7, and Cytokine. 1992 January; 4(1): 6-11). An exceptional property of sIL-6R molecules is that they act as potent agonists of IL-6 on many cell types including human cells (Taga et al, Cell. 1989 11; 58(3): 573-81, Novick et al. 1992 4(1): 6-11). Even without the intracytoplasmic domain of gp80, sIL-6R is still capable of triggering the dimerization of gp130 in response to IL-6, which in turn mediates the subsequent IL-6-specific signal transduction and biological effects (Murakami Science. 1993 Jun. 18; 260(5115): 1808-10). sIL-6R has two types of interaction with gp130 both of which are essential for the IL-6 specific biological activities (Halimi et al., Eur Cytokine Netw. 1995 May-June; 6(3): 135-43), and the active IL-6 receptor complex was proposed to be a hexameric structure formed by two gp130 chains, two IL-6R and two IL-6 ligands (Ward et al., 1994; Paonessa et al, EMBO J. 1995 May 1; 14(9): 1942-51).

In contrast to the expression of the cognate IL-6R which has a limited cellular distribution (Jones et al. 2001), expression of the trans-membrane-spanning gp130 is found in almost all organs, including heart, kidney, spleen, liver, lung, placenta, and brain (Saito et al J. Immunol. 1992 Jun. 15; 148(12): 4066-71).

There are many different examples, which show that IL-6 alone does not induce a specific activity unless the soluble IL-6R is administered. For example, IL-6 induces osteoclast formation in co-cultures of mouse bone marrow and osteoblastic cells, only when combined with the sIL-6R (Jones et al. 2001). Also, although many neuronal cells are capable of producing IL-6, they remain unresponsive to stimulation by IL-6 itself. Differentiation and survival of neuronal cells can, however, be mediated through the action of sIL-6R (Hirota J Exp Med. 1996 Jun. 1; 183(6): 2627-34. Martz Cheng, J.-G., Gadient, R. A., Patterson, P. H., Stoyan, T., Otten, U., Rose-John, S. (1998) Sympathetic neurons can produce and respond to interleukin-6. Proc. Natl. Acad. Sci. USA 95, 3251-3256).

The circulating concentrations of sIL-6R (agonist) in normal subjects are relatively high and comparable to those of soluble gp130 (a natural antagonist of IL-6), of above 10 ng/ml (Corbi et al 2000 Eur J Cardiotherac Surg. 18 (1): 98-103, Disthabanchong et al. Clin Nephrol. 2002 October; 58(4): 289-95). In contrast, the circulating concentrations of IL-6 are about or below 10 pg/ml (Kado et al. 1999 Acta Diabetol. June 36 (1-2)67-72, Corbi et al 2000. Thus the effect of IL-6 administration in vivo, alone, without co-administration with sIL-6R in disease may or may not be effective and depends on the concentration of the soluble agonist/antagonist in a particular disease and in a particular location in the body.

Chimeric molecules linking the soluble IL-6 receptor and IL-6 together have been described (Chebath et al. Eur Cytokine Netw. 1997 December; 8(4): 359-65). They have been designated IL-6R/IL-6 chimera. The chimeric IL-6R/IL-6 molecules were generated by fusing the entire coding regions of the cDNAs encoding the soluble IL-6 receptor (sIL-6R) and IL-6. Recombinant IL-6R/IL-6 chimera was produced in CHO cells (Chebath et al, Eur Cytokine Netw. 1997, WO99/02552). The IL-6R/IL-6 binds with a higher efficiency to the gp130 chain in vitro than does IL-6 with sIL-6R (Kollet et al, Blood. 1999 Aug. 1; 94(3): 923-31).

As mentioned above, interleukin-6 signaling is facilitated through the homodimerization of gp130 to the ligand-receptor complex. Intracellular signaling is subsequently triggered via activation of gp130-associated cytoplasmic tyrosine kinases (JAK1, JAK2, and TYK2) and phosphorylation of STAT1 and STAT3 (Murakami et al Science. 1993 Jun. 18; 260(5115): 1808-10. Gerhartz et al. J Biol Chem. 1996 May 31; 271(22):12991-8). In contrast, the high-affinity receptors of LIF, OSM, and CNTF activate cells by a heterodimerization between gp130 and a gp130-related protein (the LIF receptor) (Davis et al. Science. 1993 Jun. 18; 260(5115): 1805-8). Such homo- or heterodimers activate distinct but overlapping patterns of tyrosine phosphorylation through the Jak-Tyk family of cytoplasmic tyrosine kinases (Boulton et al. J Biol Chem. 1994 Apr. 15; 269(15): 11648-55). This may contribute to the different cellular responses associated with this family of proteins.

The therapeutic effect of recombinant IL-6 alone without the soluble IL-6R in an animal model of diabetes-induced neuropathy has been disclosed in patent application WO03033015. However, it is uncertain whether in a different type of peripheral neuropathy such as chemotherapy-induced peripheral neuropathy (CIPN) IL-6, administrated alone without the soluble IL-6R, is capable of a therapeutically and/or a preventive effect.

In phase I clinical trials of hrIL-6 in patients with myelodysplastic syndromes and trombocytopenia the maximum dose tolerated was found to be 3.75 μg/kg/d (Gordon et al. Blood 1995 85 (11): 3066-76.

It is uncertain whether a low dose of IL-6, which may preclude toxicity, is efficient in preventing and or curing and/or ameliorating chemotherapy-induced neuropathy.

Recombinant leukemia inhibitor factor (LIF), another gp130 activator, was tested in clinical trials for preventing CIPN caused by carboplatin/paclitaxel assessed by composite peripheral nerve electrophysiology (CPNE) score, based on nerve velocity, amplitude and H-reflex latency, vibration perception threshold and symptom scores (2003, ASCO annual meeting Abstract number 2976). In these studies either 2 or 4 μg/kg LIF were given sub coetaneous daily for 7 days starting the day prior to carboplatin/paclitaxel. The results of the clinical trials indicated that LIF was ineffective at preventing CIPN at the doses and regime tested.

Therefore, new drugs/strategies for preventing/treating peripheral neuropathy caused by a wide range of chemotherapy agents are thus needed.

SUMMARY OF THE INVENTION

The present invention relates to the use of a low dose of IL-6, or a mutein, isoform, fused protein, functional derivative, active fraction or circularly permutated derivative or a salt thereof, for the manufacture of a medicament for the prevention and/or treatment of chemotherapy-induced peripheral neuropathy.

In one embodiment of the invention, the chemotherapy-induced peripheral neuropathy is caused by at least one chemotherapeutic agent such as vincristine, cisplatin, carboplatin, or taxol.

In a further embodiment of the invention, the chemotherapeutic agent consists of a mixture of carboplatin and taxol.

In a further embodiment of the invention, the dose of IL-6, or a mutein, isoform, fused protein, functional derivative, active fraction or circularly permutated derivative or a salt thereof, is in the range of 4 to 210 µg, preferably, 7 to 140 µg or about 4, 7, 14, 28, 70 or 140 µg.

In one embodiment of the invention, the IL-6, or a mutein, isoform, fused protein, functional derivative, active fraction or circularly permutated derivative or a salt thereof is glycosylated at one or more sites while in another embodiment of the invention, the IL-6 is not-glycosylated.

In a further embodiment of the invention, the functional derivative of IL-6 comprises at least one chemical moiety, such as polyethylene glycol, attached to one or more functional groups, which occur at one or more side chains on the amino acid residues.

In one aspect, the invention provides the use of a recombinant cell producing a low dose of IL-6, or a mutein, isoform, fused protein, active fraction or circularly permutated derivative thereof, for the manufacture of a medicament for the prevention and/or treatment of chemotherapy-induced peripheral neuropathy.

In another aspect, the invention provides the use of a vector, such as a lentiviral vector, comprising the coding sequence of an IL-6 and capable of expressing a low dose of IL-6, or a mutein, isoform, fused protein, active fraction or circularly permutated derivative thereof, for the manufacture of a medicament for the prevention and/or treatment of chemotherapy-induced peripheral neuropathy.

In a further aspect, the invention provides the use of a combination of IL-6, or an isoform, mutein, fused protein, functional derivative or fragment thereof, with at least one chemotherapeutic agent, such as vincristine, cisplatin, carboplatin, taxol or a mixture of chemotherapeutic agents, preferably a mixture of carboplatin and taxol, for the manufacture of a medicament.

In one embodiment of the invention, the IL-6, or a mutein, isoform, fused protein, functional derivative, active fraction or circularly permutated derivative or a salt thereof, in said combination is glycosylated at one or more sites.

In another embodiment of the invention, the IL-6, or a mutein, isoform, fused protein, functional derivative, active fraction or circularly permutated derivative or a salt thereof, in said combination is not glycosylated.

In a further embodiment of the invention, the functional derivative of IL-6, in said combination is not glycosylated comprises at least one chemical moiety, such as a polyethylene glycol moiety, attached to one or more functional groups, which occur at one or more side chains on the amino acid residues.

In one aspect, the invention provides a method for treating and/or preventing chemotherapy-induced peripheral neuropathy, comprising administering to a patient under treatment or before treatment with at least one chemotherapeutic agent, a low dose of IL-6, or a mutein, isoform, fused protein, functional derivative, active fraction, circularly permutated derivative or a salt thereof.

In a further embodiment of the method of treatment and/or prevention in accordance with the invention, the patient is a high-risk patient to suffer of chemotherapy-induced peripheral neuropathy or the patient exhibits high levels of IL-6 receptor in the circulation.

In a further embodiment of the method of the invention, the IL-6, or a mutein, isoform, fused protein, functional derivative, active fraction or circularly permutated derivative or a salt thereof, is administered daily or three times per week for at least two weeks.

In a yet further embodiment of the method of the invention the IL-6, or a mutein, isoform, fused protein, functional derivative, active fraction or circularly permutated derivative or a salt thereof, is administered subcutaneously.

In a yet further embodiment of the method of the invention the IL-6 administration of the low doses of IL-6 is effected by endogenous gene activation (EGA), by administration of a recombinant cell producing IL-6 or by vector, such as a lentivirus, capable of expressing IL-6.

In one aspect, the invention provides a method for increasing the dose and/or prolonging the administration of at least one chemotherapeutic agent to a patient under treatment or before treatment with said chemotherapeutic agent, comprising administering a low dose of IL-6, or a mutein, isoform, fused protein, functional derivative, active fraction, circularly permutated derivative or a salt thereof, to prevent chemotherapy-induced neuropathy in said patient.

In a further embodiment of said method of the invention, the IL-6 is administered either before, during and/or after the chemotherapeutic agent.

In a further embodiment of the method of the invention, the dose of IL-6, or a mutein, isoform, fused protein, functional derivative, active fraction or circularly permutated derivative or a salt thereof, is in the range of 0.06 to 3 µg/kg body weight, preferably in the range of 0.1 to 2 µg/kg body weight or about 0.2, 0.3, 1, 2, or 3 µg/kg body weight.

In a further embodiment of the method of the invention, the dose of IL-6, or a mutein, isoform, fused protein, functional derivative, active fraction or circularly permutated derivative or a salt thereof, is in the range of 4 to 210 µg, preferably in the range of 7 to 140 µg or about 4, 7, 14, 28, 70 or 140 µg.

The invention provides also a pharmaceutical composition comprising a pharmaceutically acceptable carrier and a combination of IL-6, or an isoform, mutein, fused protein, functional derivative or fragment thereof, with at least one chemotherapeutic agent such as vincristine, cisplatin, carboplatin or taxol or a mixture thereof such as the mixture of carboplatin and taxol.

In further embodiments of the invention, the IL-6, or a mutein, isoform, fused protein, functional derivative, active fraction or circularly permutated derivative or a salt thereof, in the pharmaceutical composition is glycosylated at one or more sites or the IL-6, or a mutein, isoform, fused protein, functional derivative, active fraction or circularly permutated derivative or a salt thereof, in the pharmaceutical composition is not glycosylated.

In a further embodiment of the invention, the functional derivative of IL-6 in the pharmaceutical composition comprises at least one chemical moiety attached to one or more functional groups, such as a polyethylene glycol moiety, which occur at one or more side chains on the amino acid residues.

In a further embodiment of the invention the pharmaceutical composition further comprises a neuroprotective drug, such as nerve growth factor (NGF) or glutamine.

More specifically, in one embodiment of the invention, the amount of IL-6, or a mutein, isoform, fused protein, functional derivative, active fraction or circularly permutated derivative or a salt thereof, in the pharmaceutical composition is in the range of 4 to 210 µg, preferably in the range of 7 to 140 µg, or about 4, 7, 14, 28, 70 or 140 µg.

In one aspect, the invention provides a kit comprising: one or more containers comprising each a chemotherapeutic agent; one container comprising IL-6 or a mutein, isoform, fused protein, functional derivative, active fraction or circularly permutated derivative or a salt thereof; and instructions for administration of said chemotherapeutic agent and said IL-6 for the prevention and/or treatment of chemotherapy-induced peripheral neuropathy.

In one embodiment, the kit according to the invention contains two containers comprising each a chemotherapeutic agent, one container comprising carboplatin and another container comprising taxol.

In a further embodiment of the kit of the invention, the amount of IL-6, or a mutein, isoform, fused protein, functional derivative, active fraction or circularly permutated derivative or a salt thereof, in each container is in the range of 4 to 210 mg, preferably in the range of 7 to 140 µg, or about 4, 7, 14, 28, 70 or 140 µg.

In a yet further embodiment, the kit of the invention further comprises a container comprising a neuroprotective drug such as neural growth factor (NGF) or glutamine.

*p<0.05 Mean±s.e.m (versus control/vehicle; Dunnett's test).

Figure 3:
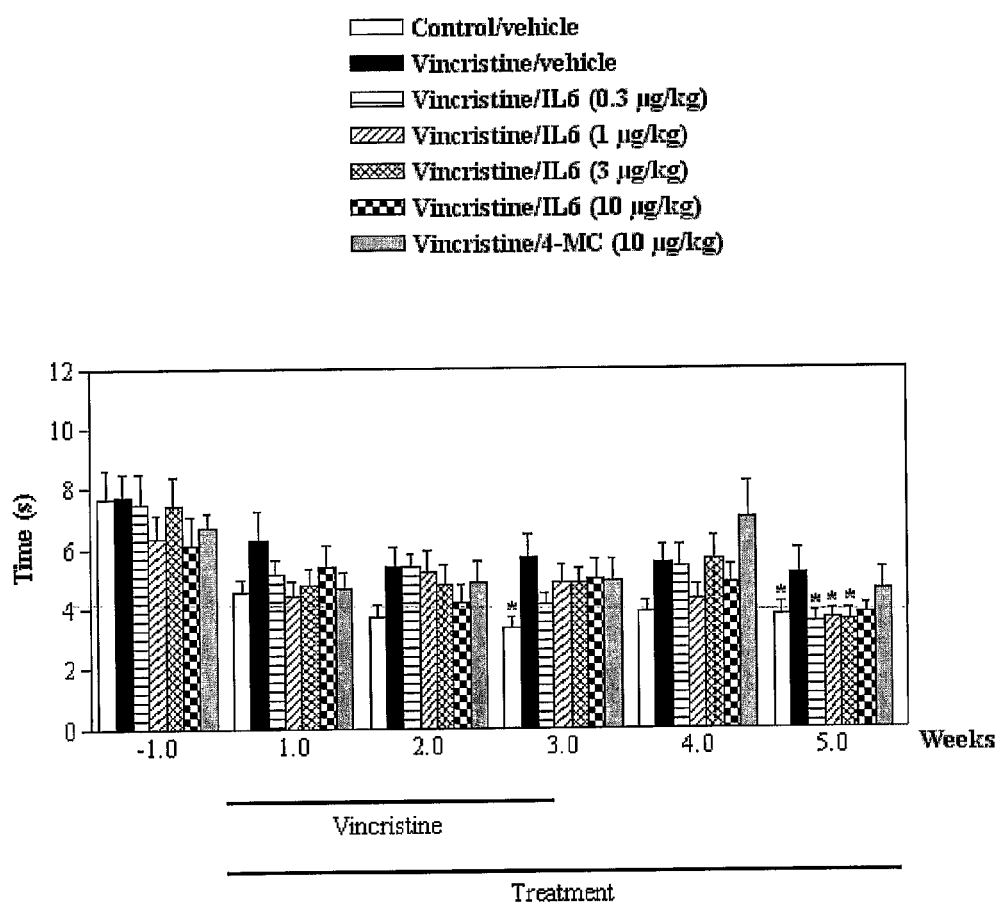

FIG. 3 shows prophylactic effect of IL-6 on vincristine-mediated neuropathy manifested by prevention of vincristine-induced nociception loss. The figure shows results of hot plate tests in vincristine-treated versus vincristine-IL-6 co-administrated at the indicated doses, or vincristine-4-MC co-administrated rats.

*p<0.05 Mean±s.e.m (versus control/vehicle; Dunnett's test).

Figure 4:
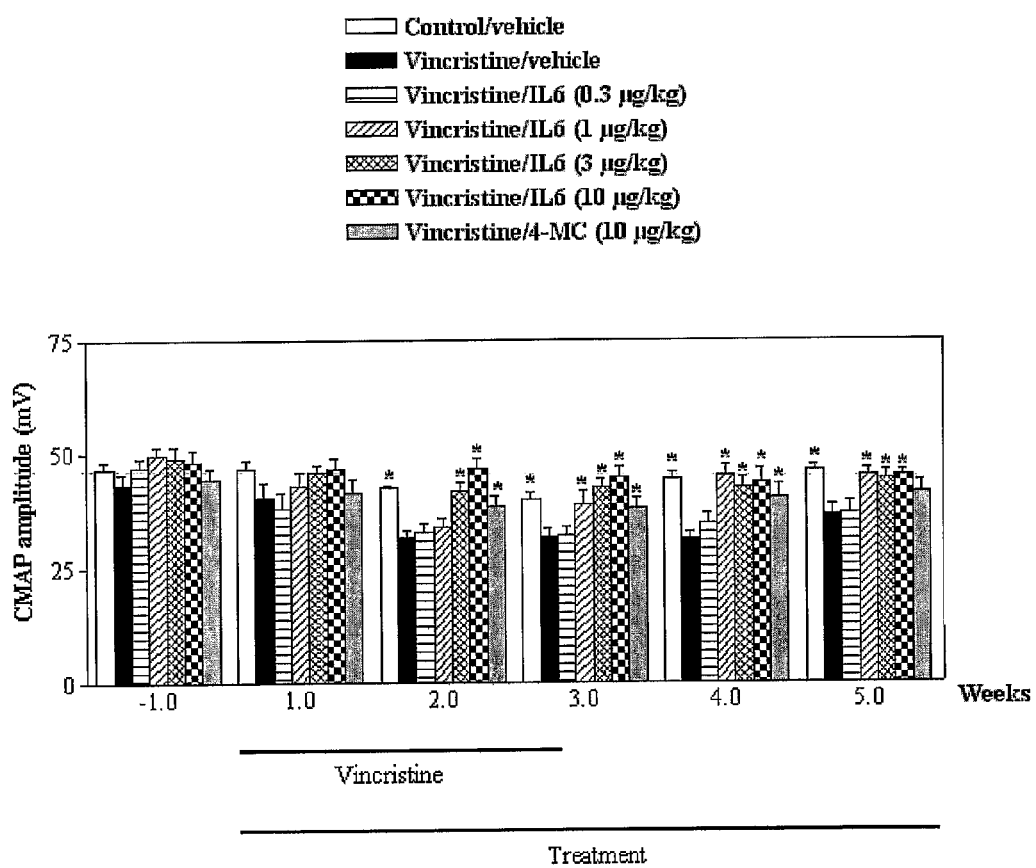

FIG. 4 shows prophylactic effect of IL-6 on vincristine-mediated neuropathy manifested by prevention of vincristine-induced impairment of fiber/nerve function. The figure shows amplitudes of compound muscular action potential (CAMP) in vincristine-treated versus vincristine-IL-6 co-administrated at the indicated doses, or vincristine-4-MC co-administrated rats.

*p<0.05 Mean±s.e.m (versus control/vehicle; Dunnett's test).

Figure 5:
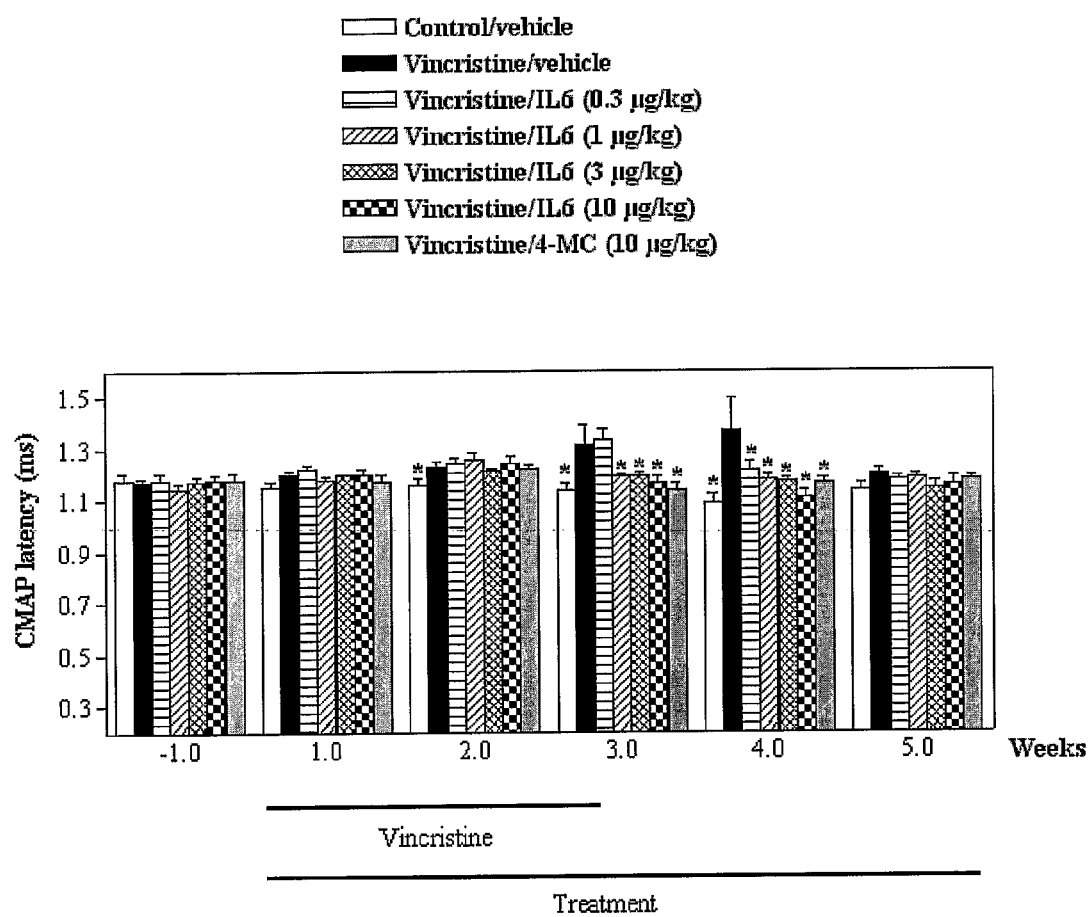

FIG. 5 shows prophylactic effect of IL-6 on vincristine-mediated neuropathy manifested by prevention of vincristine-induced impairment of fiber/nerve function. The figure shows latency of CAMP in vincristine-treated versus vincristine-IL-6 co-administrated at the indicated doses, or vincristine-4-MC co-administrated rats.

*p<0.05 Mean±s.e.m (versus control/vehicle; Dunnett's test).

Figure 6:
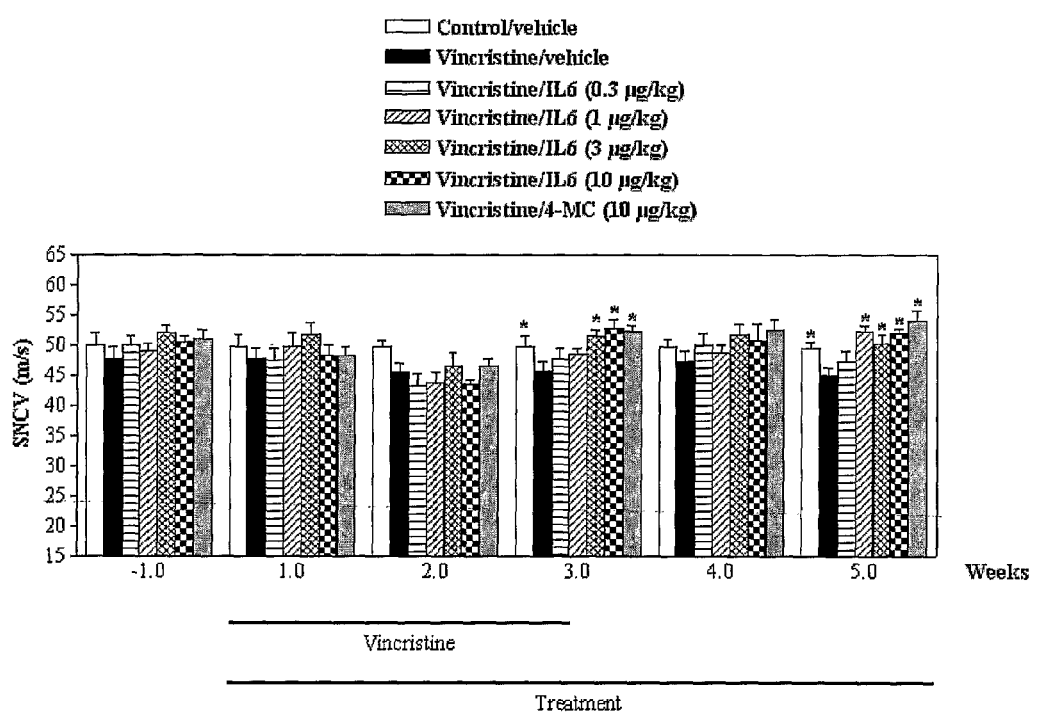

FIG. 6 shows prophylactic effect of IL-6 on vincristine-mediated neuropathy manifested by prevention of vincristine-mediated impairment of fiber/nerve function. The figure shows sensitive nerve conduction velocity (SNCV) in vincristine-treated versus vincristine-IL-6 co-administrated at the indicated doses, or vincristine-4-MC co-administrated rats.

*p<0.05 Mean±s.e.m (versus control/vehicle; Dunnett's test).

Figure 7:
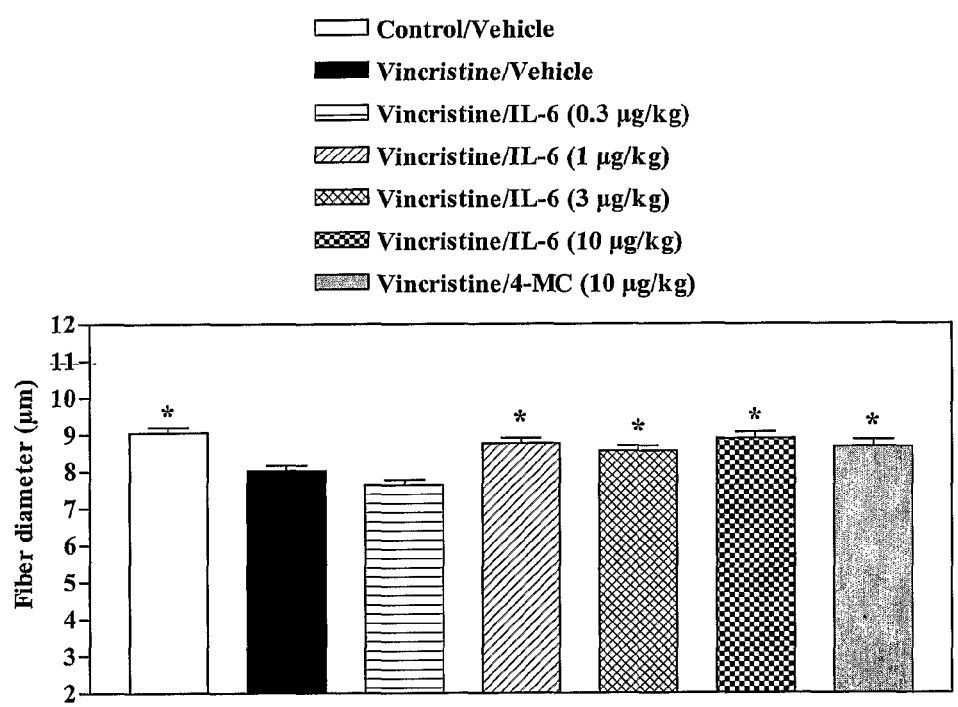

FIG. 7 shows prophylactic effect of IL-6 on vincristine-mediated neuropathy manifested by prevention of vincristine-mediated impairment of fiber/nerve morphology. The figure shows fiber diameter of sciatic nerves harvested from vincristine-treated versus vincristine-IL-6 co-administrated at the indicated doses, or vincristine-4-MC co-administrated rats.

*p<0.05 Mean±s.e.m (versus control/vehicle; Dunnett's test).

Figure 8:
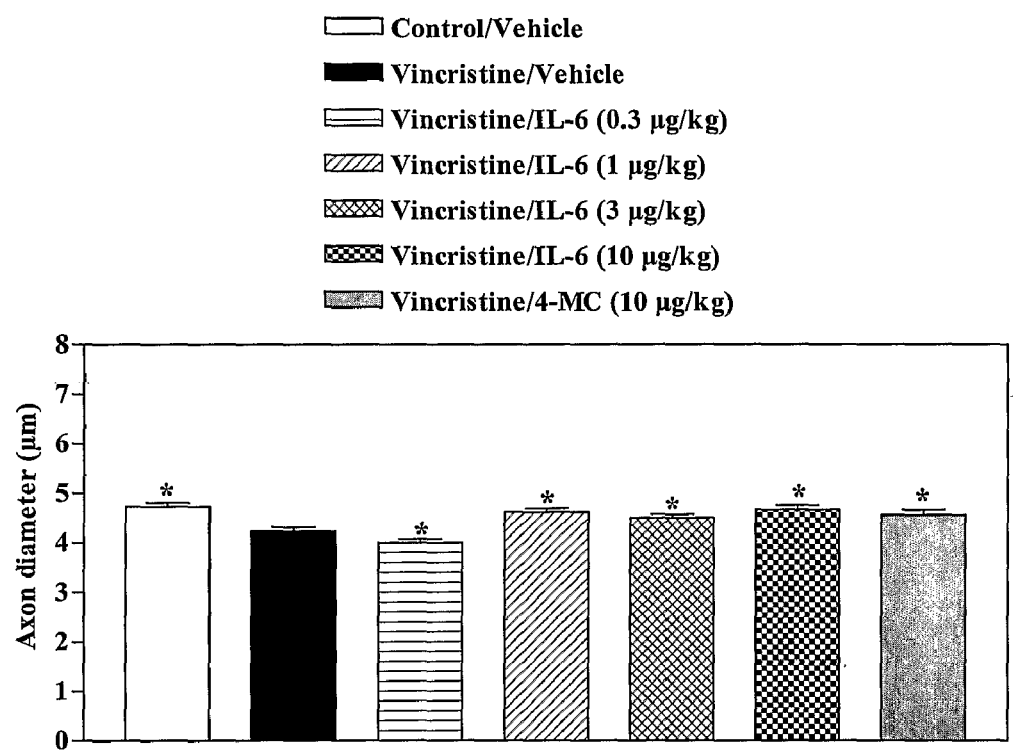

FIG. 8 shows prophylactic effect of IL-6 on vincristine-mediated neuropathy manifested by prevention of vincristine-mediated impairment of fiber/nerve morphology. The figure shows axon diameter of sciatic nerves harvested from vincristine-treated versus vincristine-IL-6 co-administrated at the indicated doses, or vincristine-4-MC co-administrated rats.

*p<0.05 Mean±s.e.m (versus control/vehicle; Dunnett's test).

Figure 9:
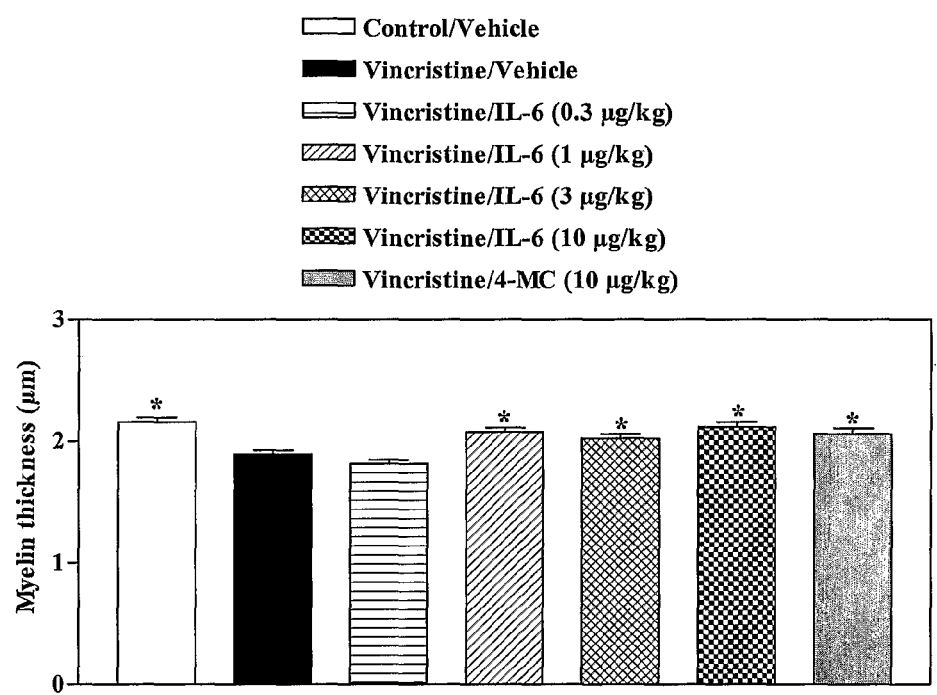

FIG. 9 shows prophylactic effect of IL-6 on vincristine-mediated neuropathy manifested by prevention of vincristine-mediated loss of myelin. The figure shows myelin thickness of sciatic nerves harvested from vincristine-treated versus vincristine-IL-6 co-administrated at the indicated doses, or vincristine-4-MC co-administrated rats.

*p<0.05 Mean±s.e.m (versus control/vehicle; Dunnett's test).

Figure 10:
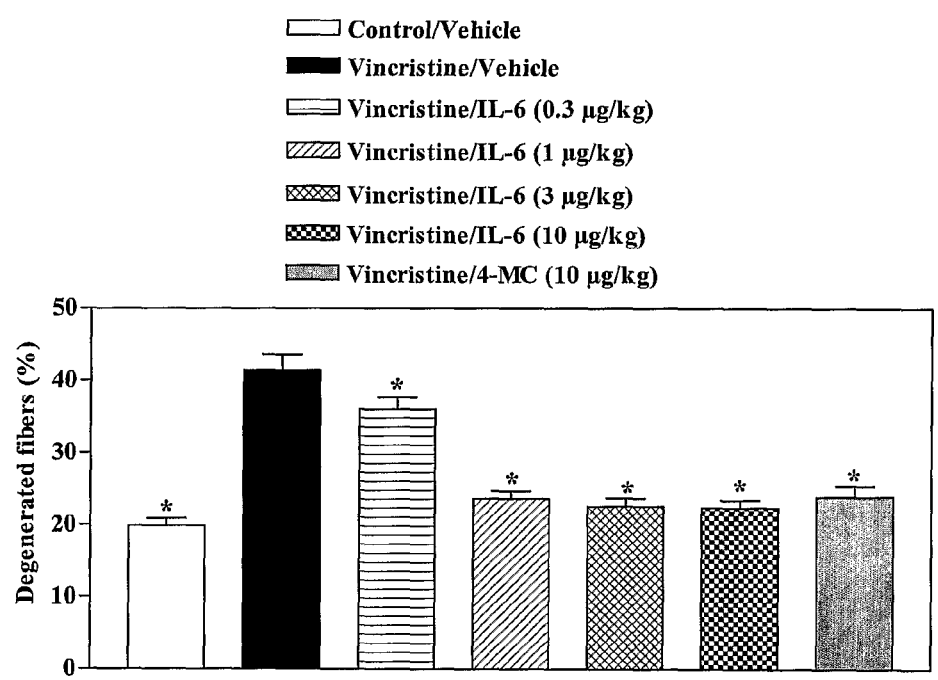

FIG. 10 shows prophylactic effect of IL-6 on vincristine-mediated neuropathy manifested by prevention of vincristine mediated fiber degeneration. The figure shows percentages of degenerated fibers in samples harvested from vincristine-treated versus vincristine-IL-6 co-administrated at the indicated doses, or vincristine-4-MC co-administrated rats.

*p<0.05 Mean±s.e.m (versus control/vehicle; Dunnett's test).

Figure 11:
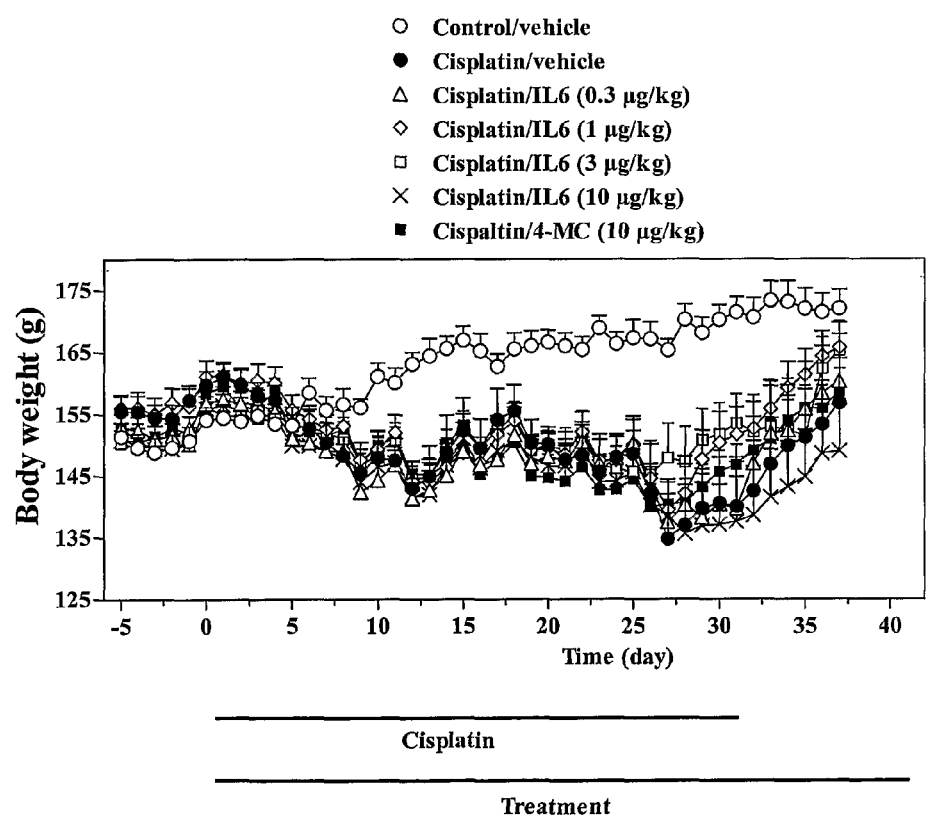
Figure 12:
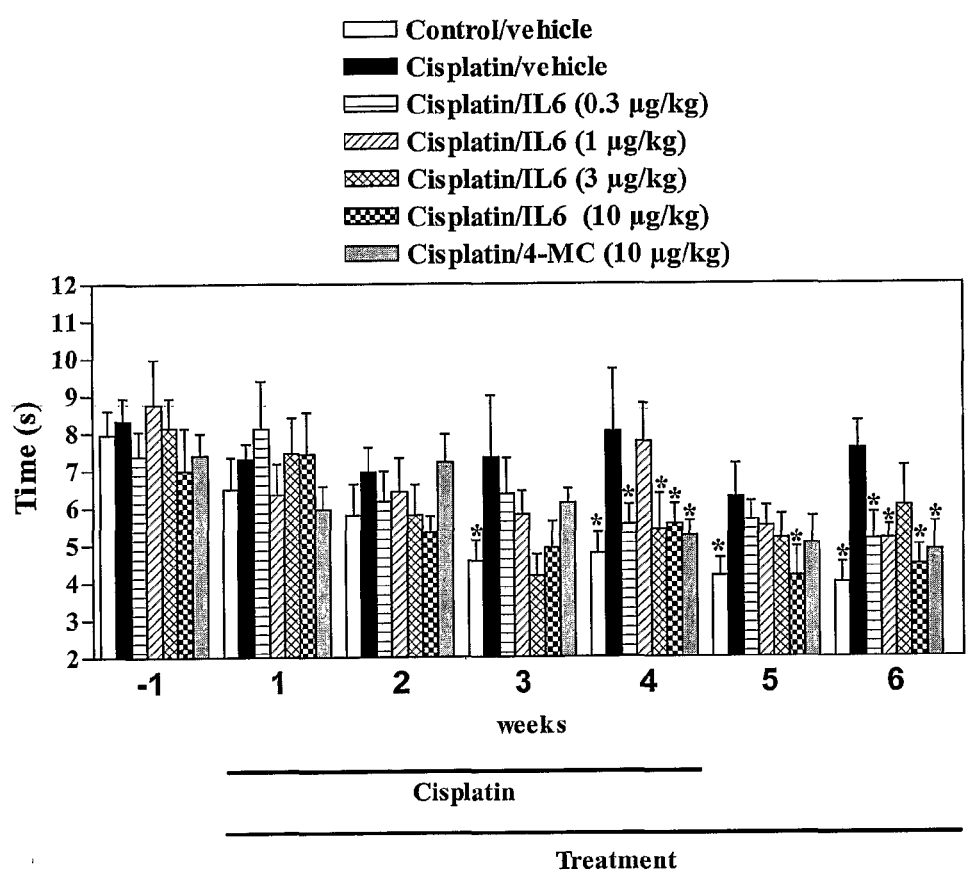

FIG. 11 shows the effect of cisplatin, cisplatin-IL-6 co-administration at the indicated doses or cisplatin-4-MC co-administration in body weight of rats. Mean±s.e.m FIG. 12 shows prophylactic effect of IL-6 on cisplatin-mediated neuropathy manifested by prevention of cisplatin mediated nociception loss. The figure shows results of hot plate tests from cisplatin-treated versus cisplatin-IL-6 co-administrated at the indicated doses, or cisplatin-4-MC co-administrated rats.

*p<0.05 (versus cisplatine/vehicle).

Figure 13:
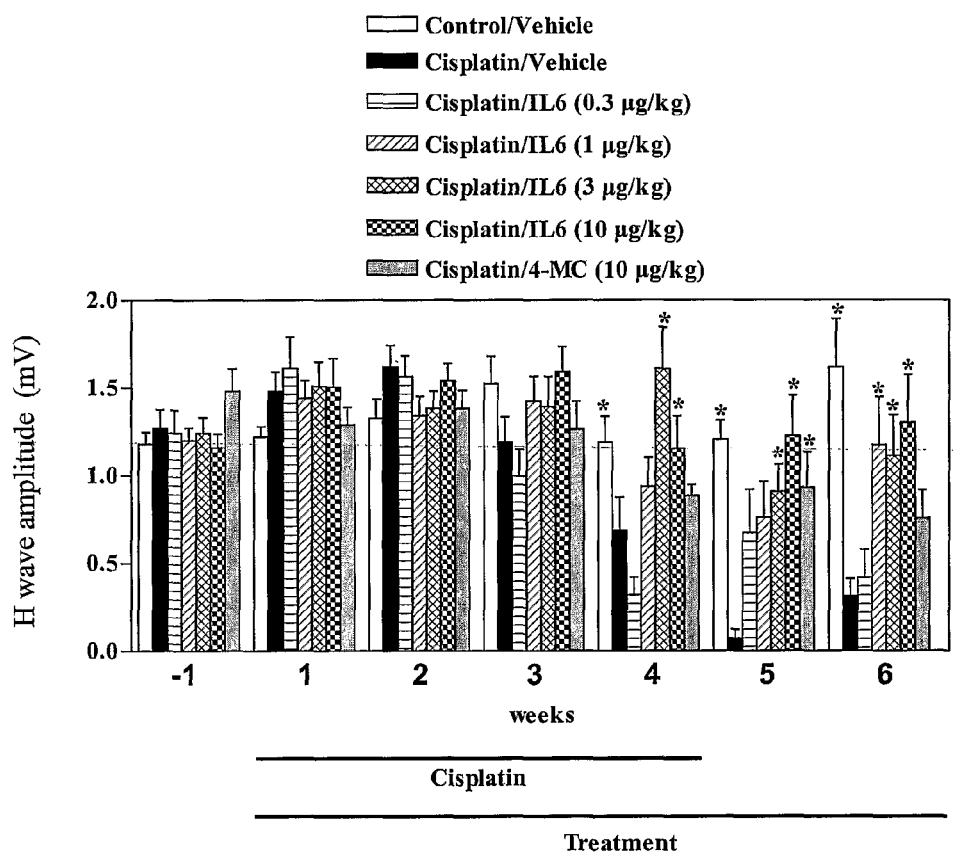

FIG. 13 shows prophylactic effect of IL-6 on cisplatin-mediated neuropathy manifested by prevention of cisplatin-mediated impairment of fiber/nerve function. The figure shows the amplitude H wave in cisplatin-treated versus cisplatin-IL-6 co-administrated at the indicated doses, or cisplatin-4-MC co-administrated rats. *p<0.05 (versus cisplatine/vehicle).

Figure 14:
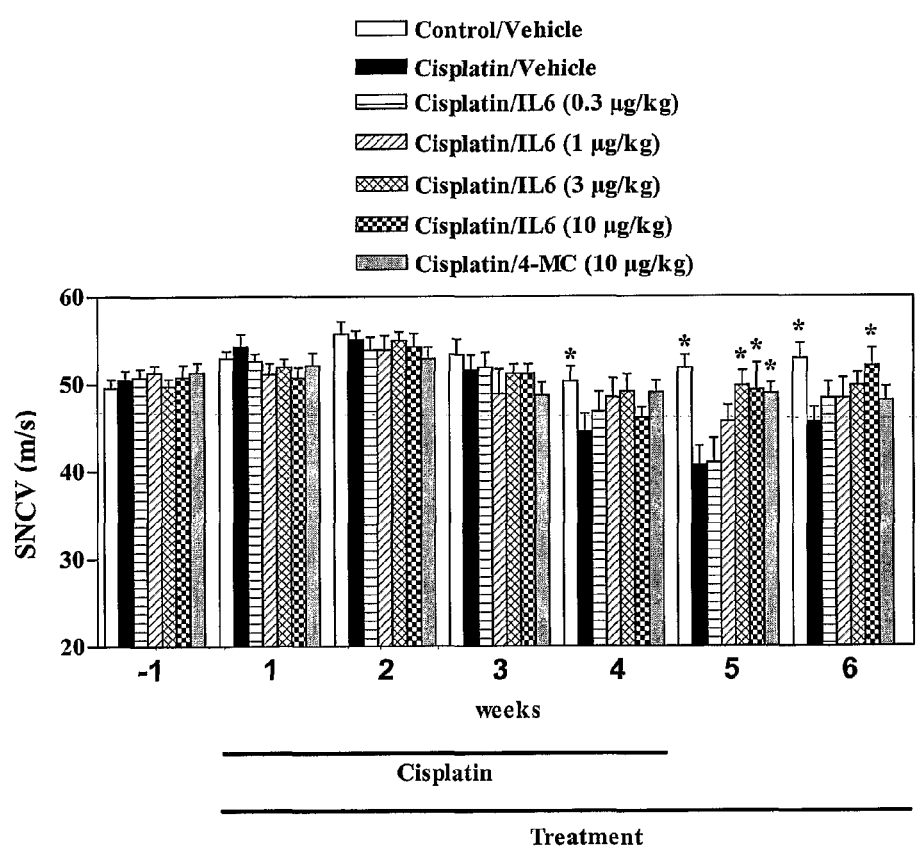

FIG. 14 shows prophylactic effect of IL-6 on cisplatin-mediated neuropathy manifested by prevention of cisplatin-mediated impairment of fiber/nerve function. The figure shows SNCV in cisplatin-treated versus cisplatin-IL-6 co-administrated at the indicated doses, or cisplatin-4-MC co-administrated rats. Mean±s.e.m *p<0.05 (versus cisplatine/vehicle).

Figure 15:
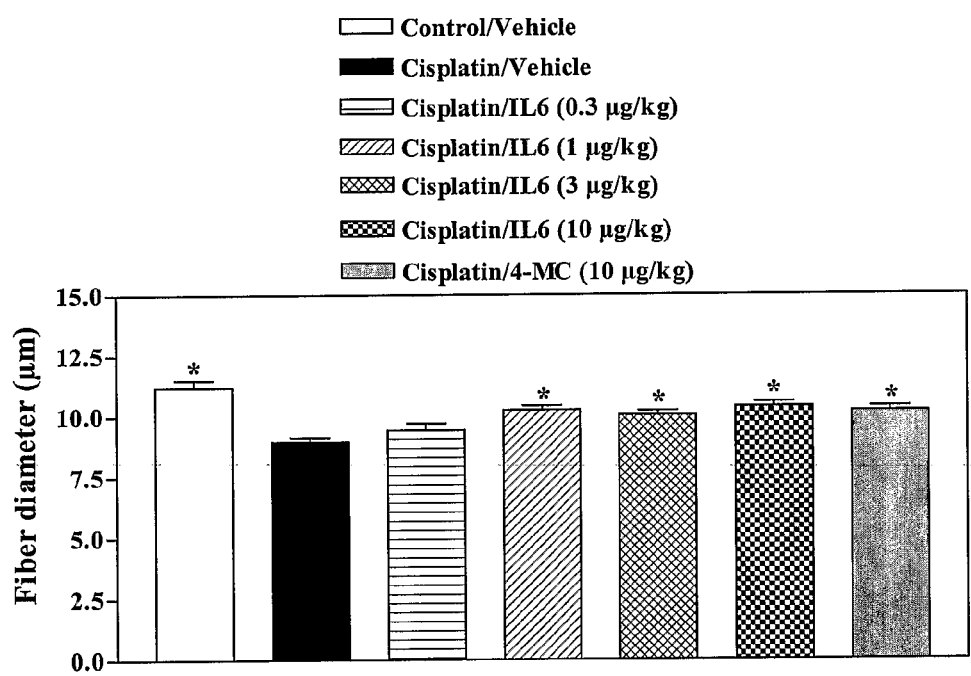

FIG. 15 shows prophylactic effect of IL-6 on cisplatin-mediated neuropathy manifested by prevention of cisplatin-mediated impairment of fiber morphology. The figure shows fiber diameter of sciatic nerves harvested from cisplatin-treated versus cisplatin-IL-6 co-administrated at the indicated doses, or cisplatin-4-MC co-administrated rats.

Figure 16:
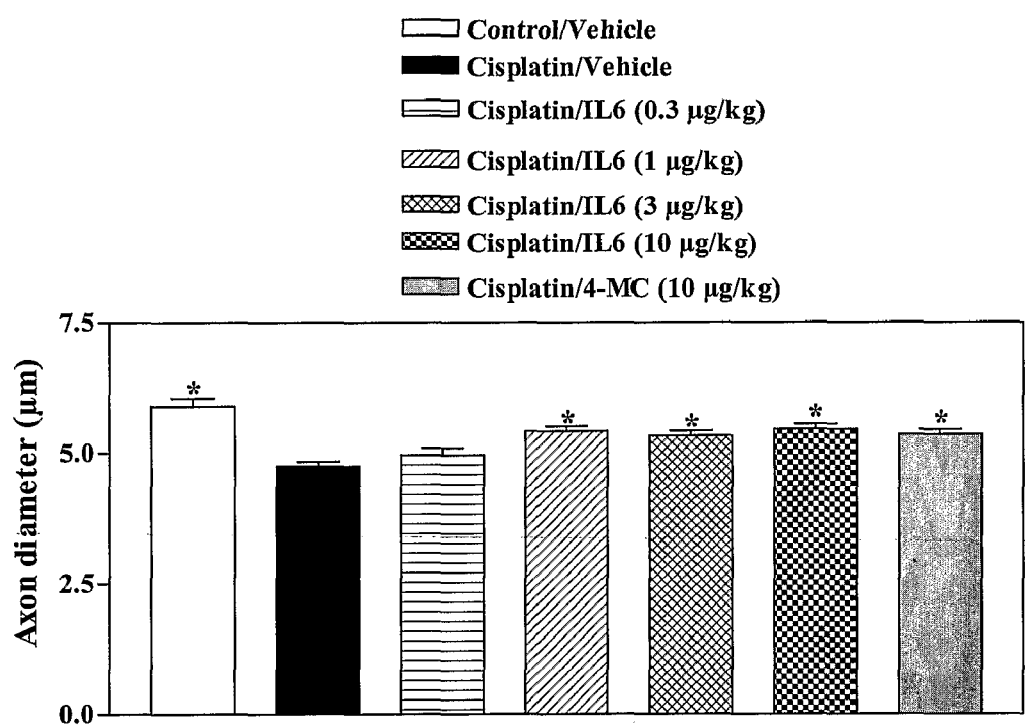
Figure 17:
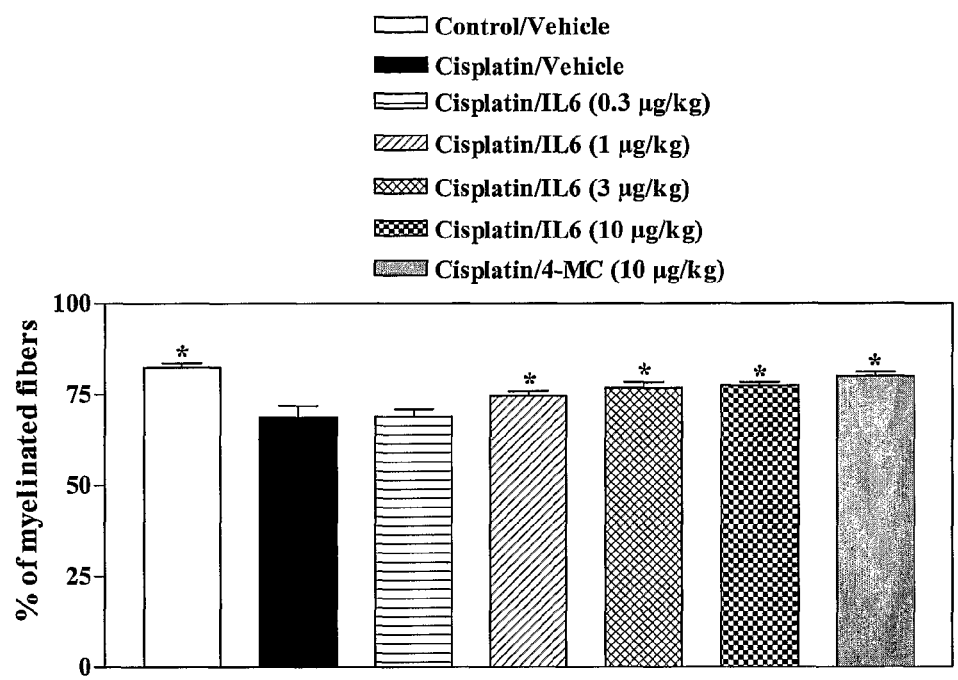

FIG. 16 shows prophylactic effect of IL-6 on cisplatin-mediated neuropathy manifested by prevention of cisplatin-mediated impairment of nerve morphology. The figure shows axon diameter of sciatic nerves harvested from cisplatin-treated versus cisplatin-IL-6 co-administrated at the indicated doses, or cisplatin-4-MC co-administrated rats, FIG. 17 shows prophylactic effect of IL-6 on cisplatin-mediated neuropathy manifested by prevention of cisplatin-mediated loss of myelin. The figure shows percentages of myelinated fibers in samples harvested from cisplatin-treated versus cisplatin-IL-6 co-administrated at the indicated doses, or cisplatin-4-MC co-administrated rats.

Figure 18:
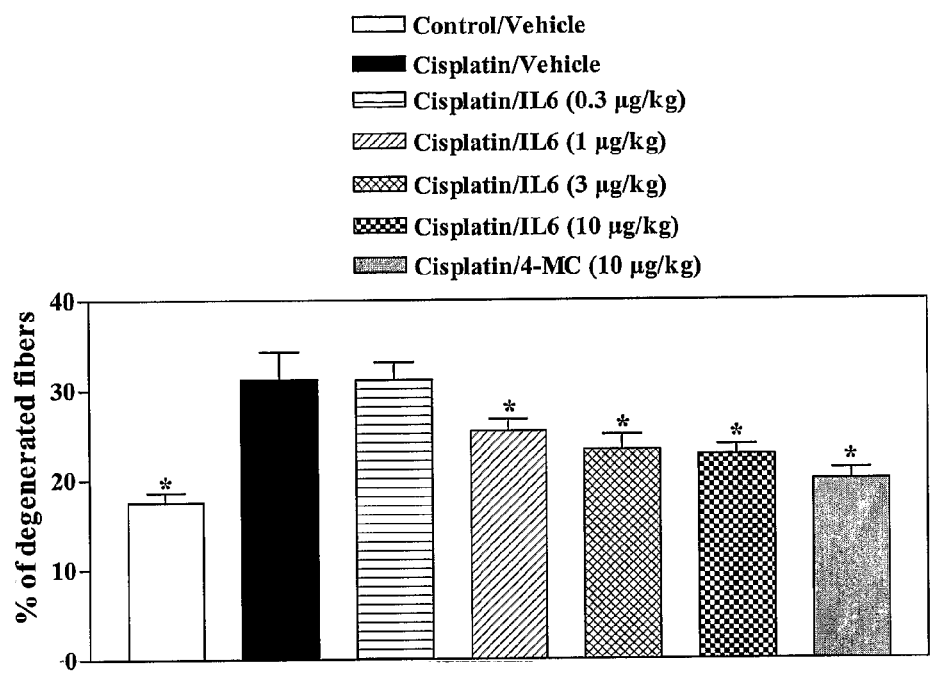

FIG. 18 shows prophylactic effect of IL-6 on cisplatin-mediated neuropathy manifested by prevention of cisplatin mediated fiber degeneration. The figure shows percentages of degenerated fibers harvested from cisplatin-treated versus cisplatin-IL-6 co-administrated at the indicated doses, or cisplatin-4-MC co-administrated rats.

Figure 19:
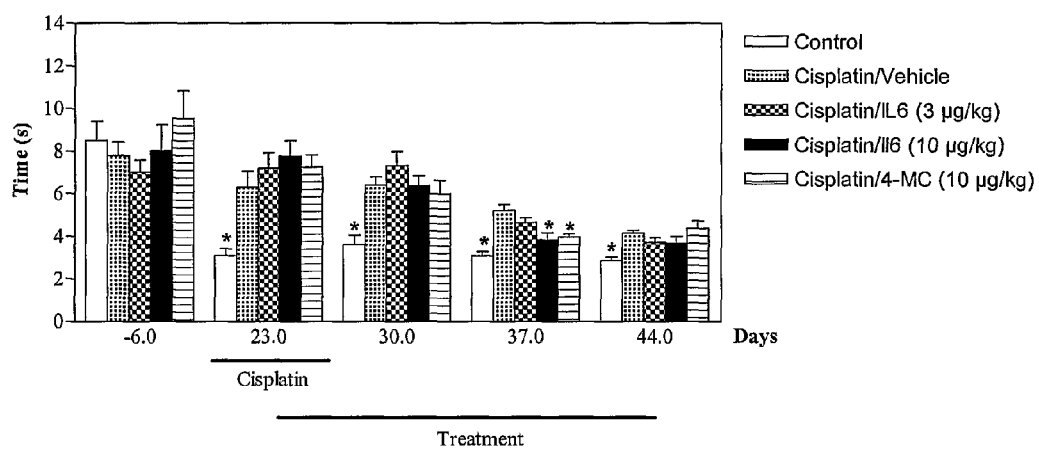

FIG. 19 shows therapeutic effect of IL-6 on cisplatin-mediated neuropathy manifested by amelioration of cisplatin-mediated induction of nociception loss. The figure shows results of hot plate tests in cisplatin-treated versus cisplatin-IL-6 co-administrated at the indicated doses, or cisplatin-4-MC co-administrated rats.

Figure 20:
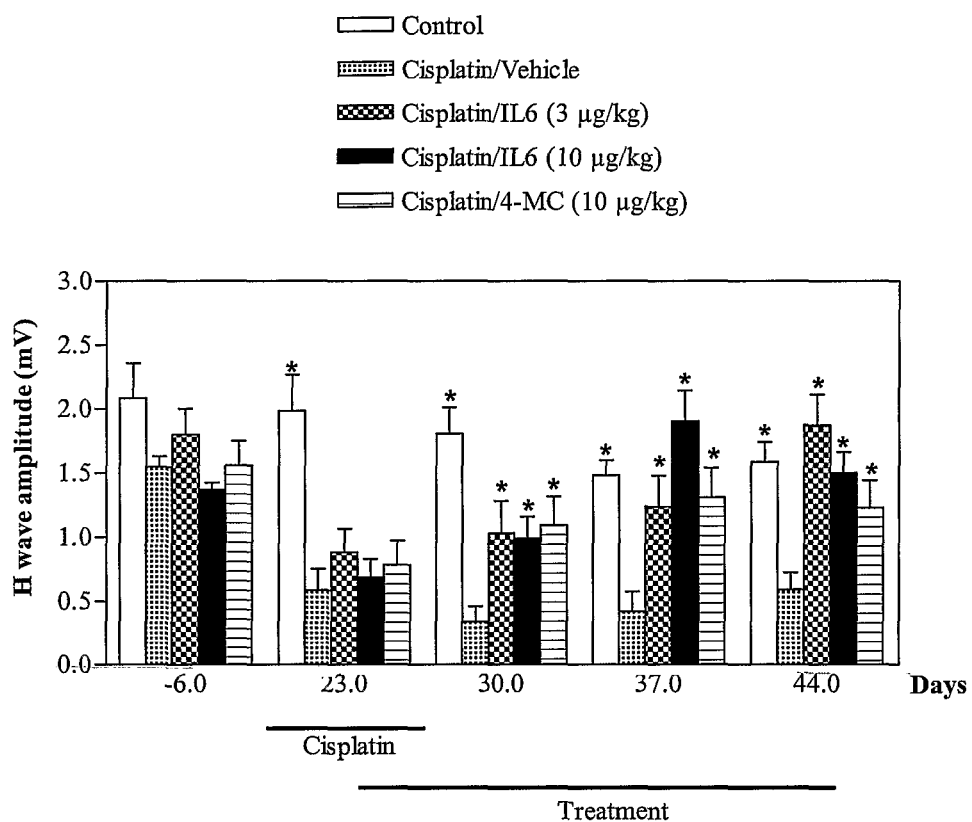

FIG. 20 shows therapeutic effect of IL-6 on cisplatin-mediated neuropathy manifested by amelioration of cisplatin-mediated impairment of fiber/nerve function. The figure shows the amplitude of H wave in cisplatin-treated versus cisplatin-IL-6 co-administrated at the indicated doses, or cisplatin-4-MC co-administrated rats.

Figure 21:
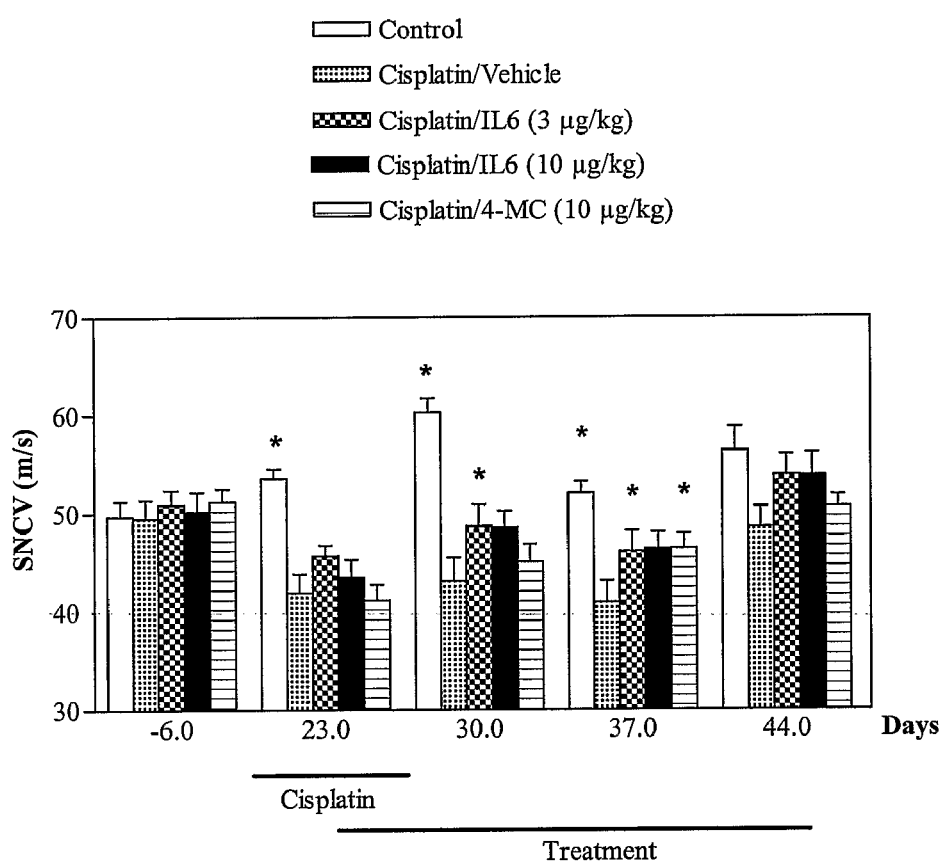

FIG. 21 shows therapeutic effect of IL-6 on cisplatin-mediated neuropathy manifested by amelioration of cisplatin-mediated impairment of fiber/nerve function. The figure shows SNCV in cisplatin-treated versus cisplatin-IL-6 co-administrated at the indicated doses, or cisplatin-4-MC co-administrated rats.

Figure 22:
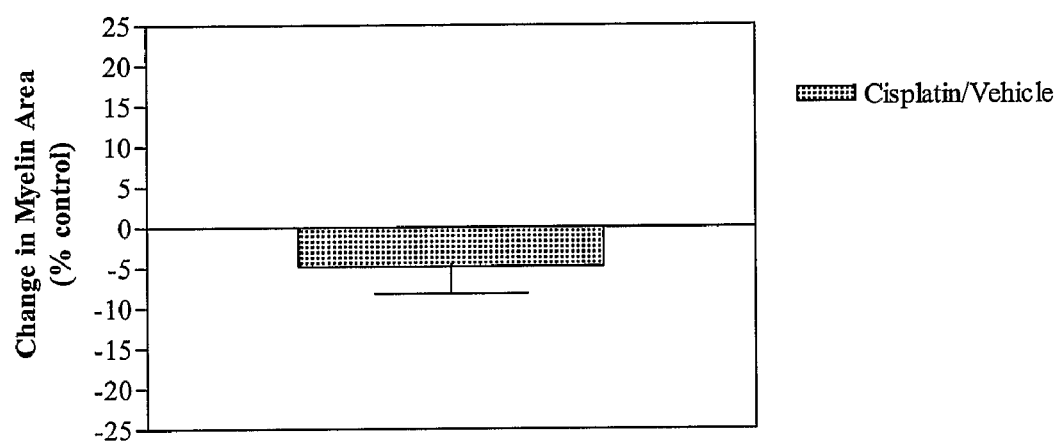

FIG. 22 shows changes in myelin area in samples harvested from cisplatin-treated group of rats.

Figure 23:
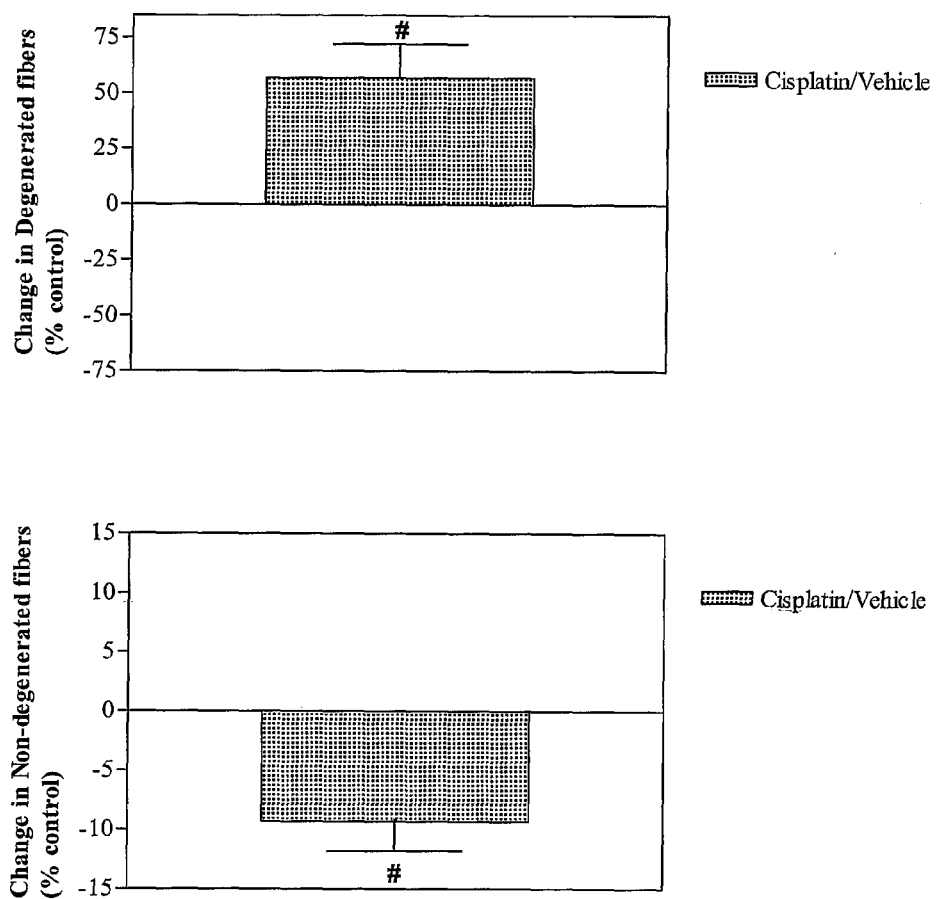

FIG. 23 A shows changes in degenerated fibers in samples harvested from cisplatin-treated group of rats.

FIG. 23 B shows changes in non-degenerated fibers in samples harvested from cisplatin-treated group of rats.

Figure 24:
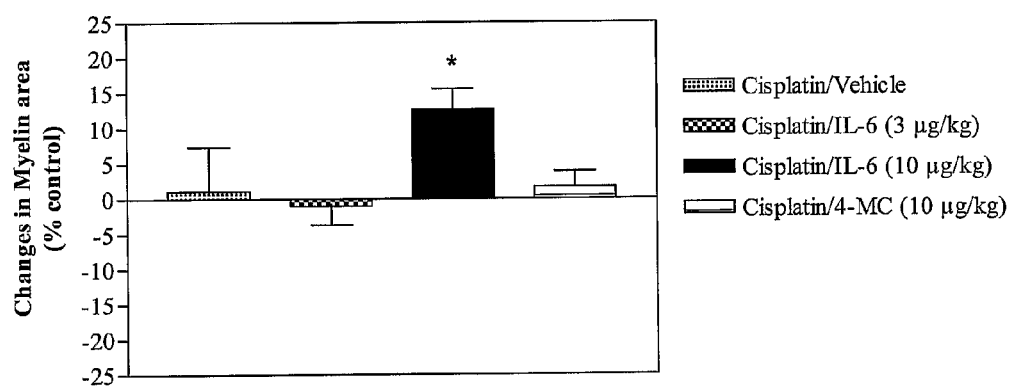

FIG. 24 shows therapeutic effect of IL-6 on cisplatin-mediated neuropathy manifested by amelioration of cisplatin-mediated loss of myelin. The results show myelin area in samples harvested from cisplatin-treated rats and cisplatin-treated rats administered with IL-6 or 4-MC.

Figure 25:
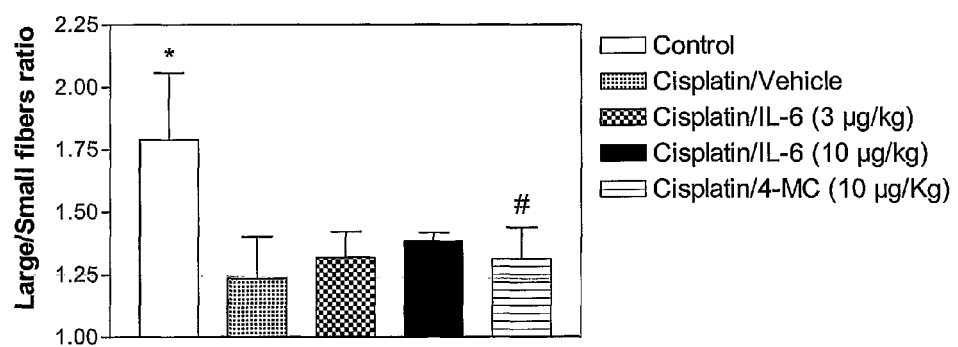

FIG. 25 shows therapeutic effect of IL-6 on cisplatin mediated neuropathy manifested by amelioration of cisplatin mediated changes of the large/small fibers ratio in samples harvested from cisplatin-treated rats and cisplatin-treated rats administered with IL-6 or 4-MC.

FIG. 26A shows therapeutic effect of IL-6 on cisplatin-mediated neuropathy manifested by amelioration of cisplatin mediated fiber degeneration. The figures show changes in degenerated fibers in samples harvested from cisplatin-treated group of rats and cisplatin-treated rats administered with IL-6 or 4-MC.

Figure 26:
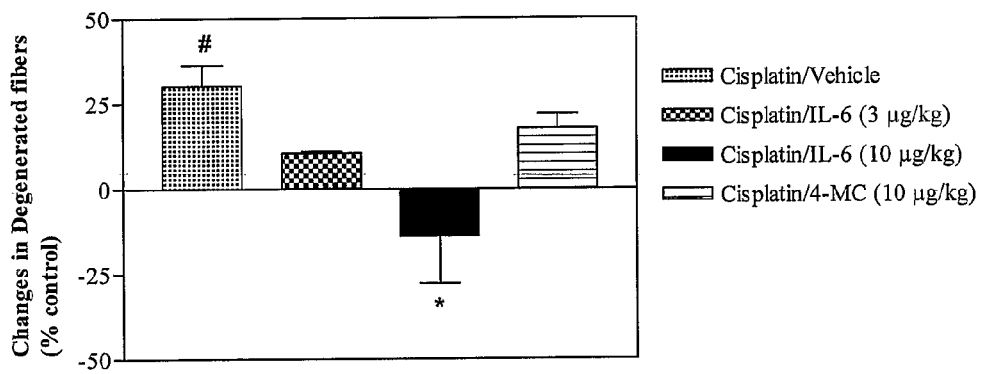
Figure 26:
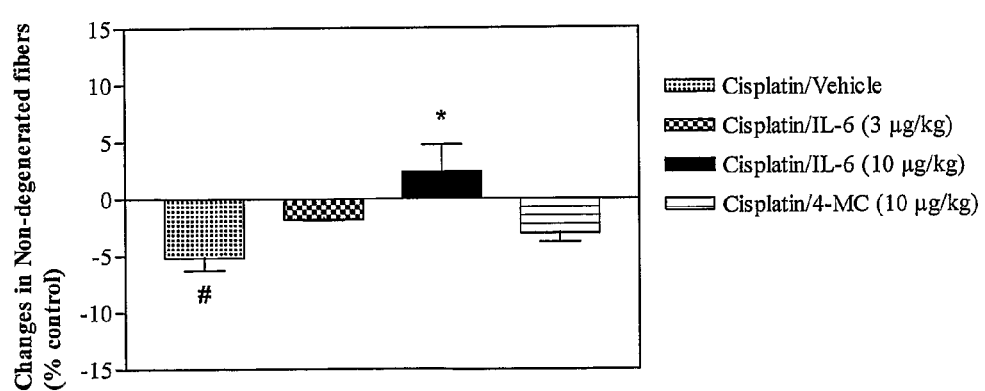

FIG. 26 B shows the therapeutic effect of IL-6 on cisplatin-mediated neuropathy manifested by amelioration of cisplatin mediated fiber degeneration. The figure shows changes in non-degenerated fibers in samples harvested from cisplatin-treated group of rats and cisplatin-treated rats treated with IL-6 or 4-MC.

Figure 27:
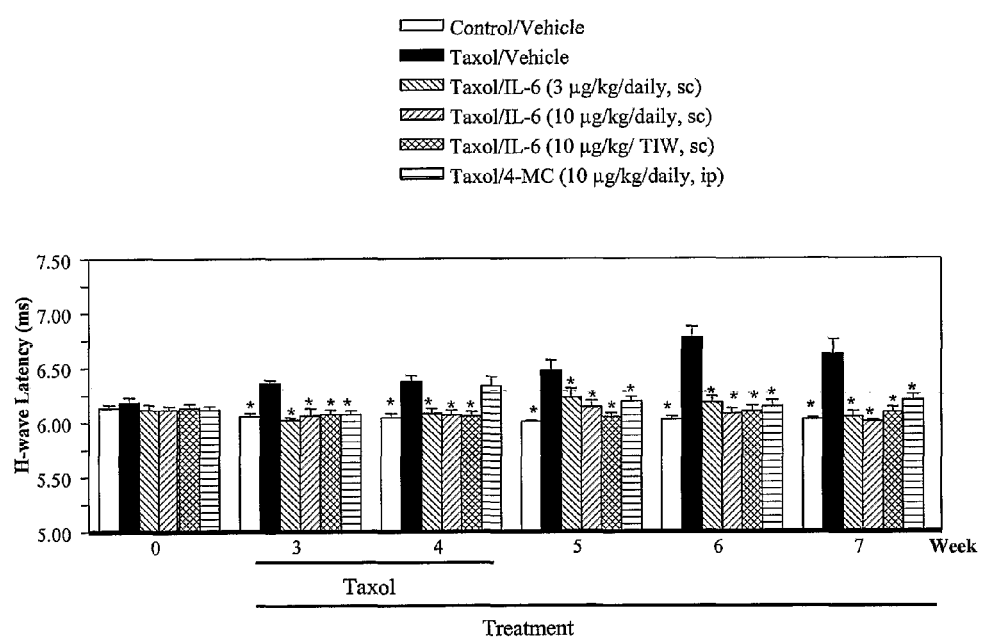

FIG. 27 shows therapeutic effect of IL-6 on taxol-mediated neuropathy manifested by amelioration of taxol mediated fiber degeneration. The figure shows H-wave latency a in group of rats treated with taxol and taxol-treated rats administered with IL-6 or 4-MC.

Figure 28:
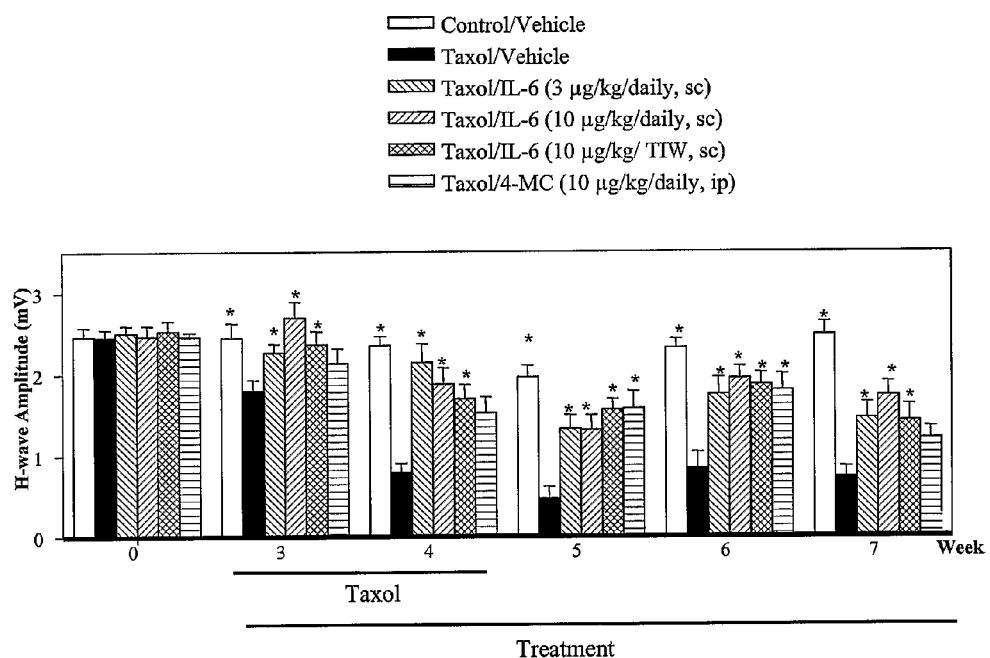

FIG. 28 shows prophylactic effect of IL-6 on taxol-mediated neuropathy manifested by prevention of H-wave decrease in amplitude. The figure shows H-wave amplitudes in group of rats treated with taxol and cisplatin-taxol rats administrated with IL-6 or 4-MC.

Figure 29:
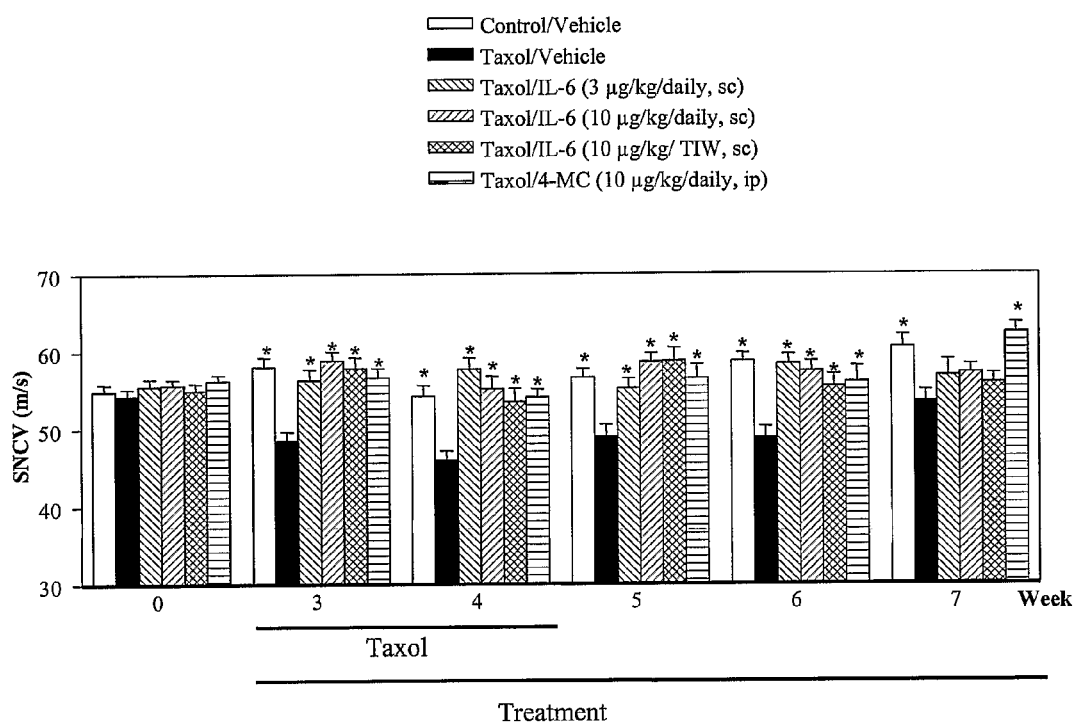
Figure 30:
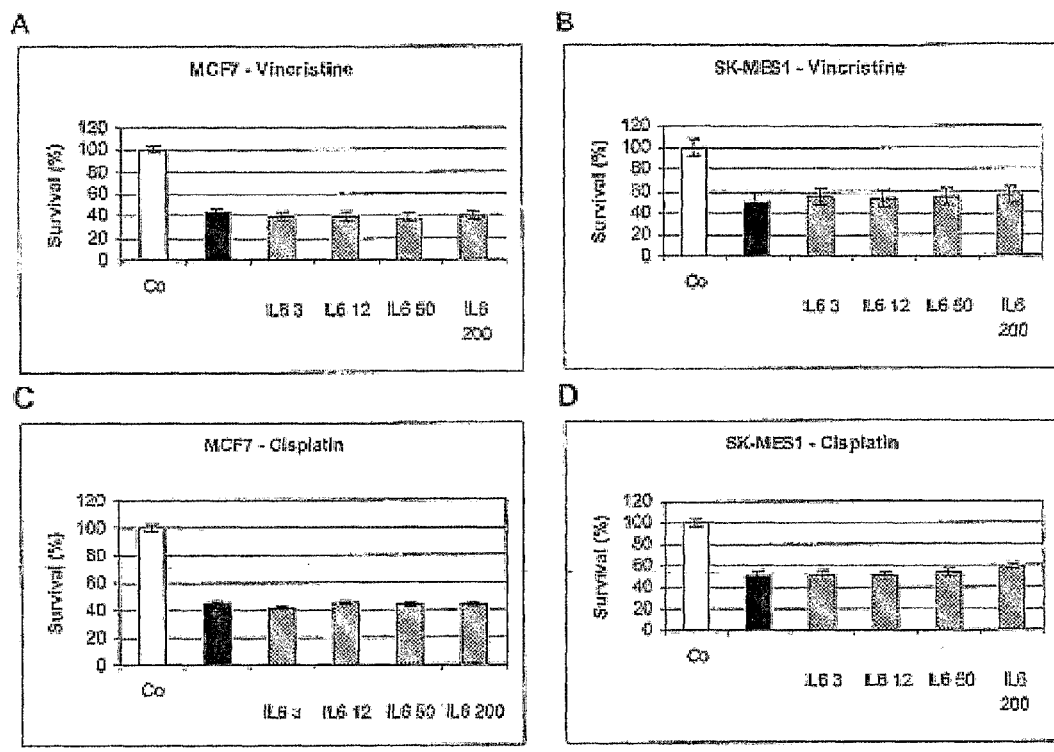

FIG. 29 shows prophylactic effect of IL-6 on taxol-mediated neuropathy manifested by prevention of taxol mediated SNCV decrease. The figure shows SNCV in group of rats treated with taxol and cisplatin-taxol rats administered with IL-6 or 4-MC FIG. 30 shows the effects of IL-6 on the anti-proliferative effects of vincristine, cisplatin, carboplatin and taxol in MCf-7 or SK-MES 1 cells. A-MCF7-vincristine, B-SK-MES-1-vincristine, C-MCF-7 cisplatin, D-SK-MES1-Cisplatin, E-MCF-7-taxol, F-SK-MES1-taxol, G-MCF7-taxol+carboplatin, H-SK-MES-taxol+carboplatin, I-MCF7-carboplatin and J-SK-MES 1-carboplatin.

Figure 31:
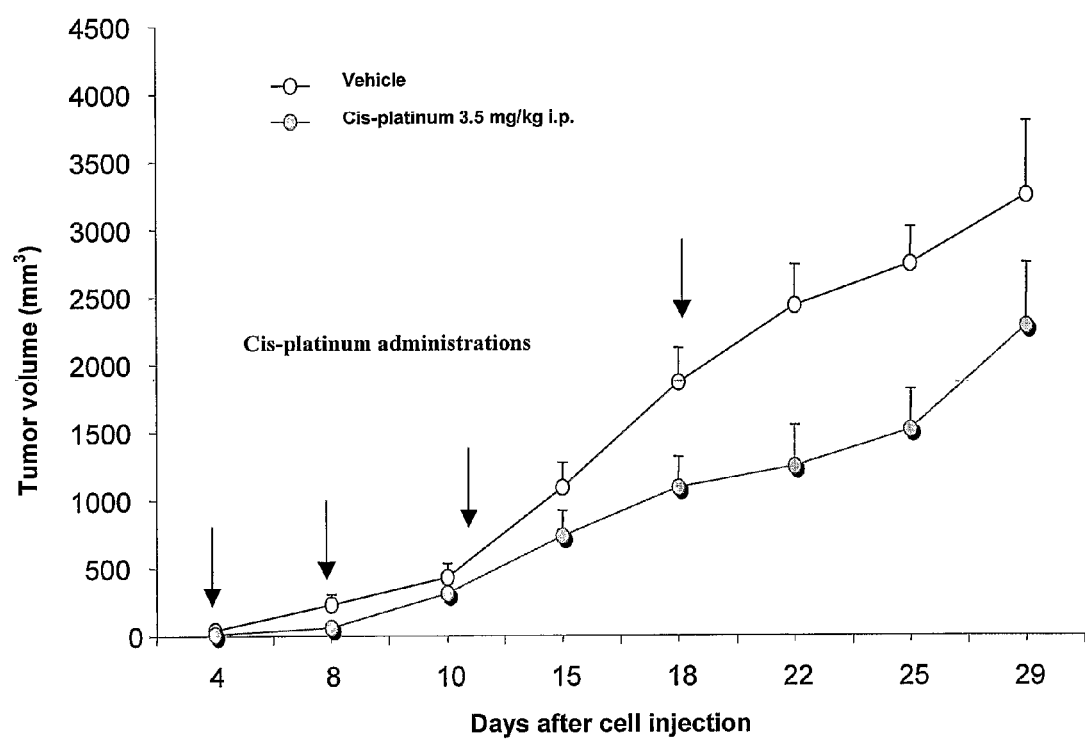

FIG. 31 shows the effect of cis-platinum on human WiDr colon carcinoma tumor growth in nude mice.

Figure 32:
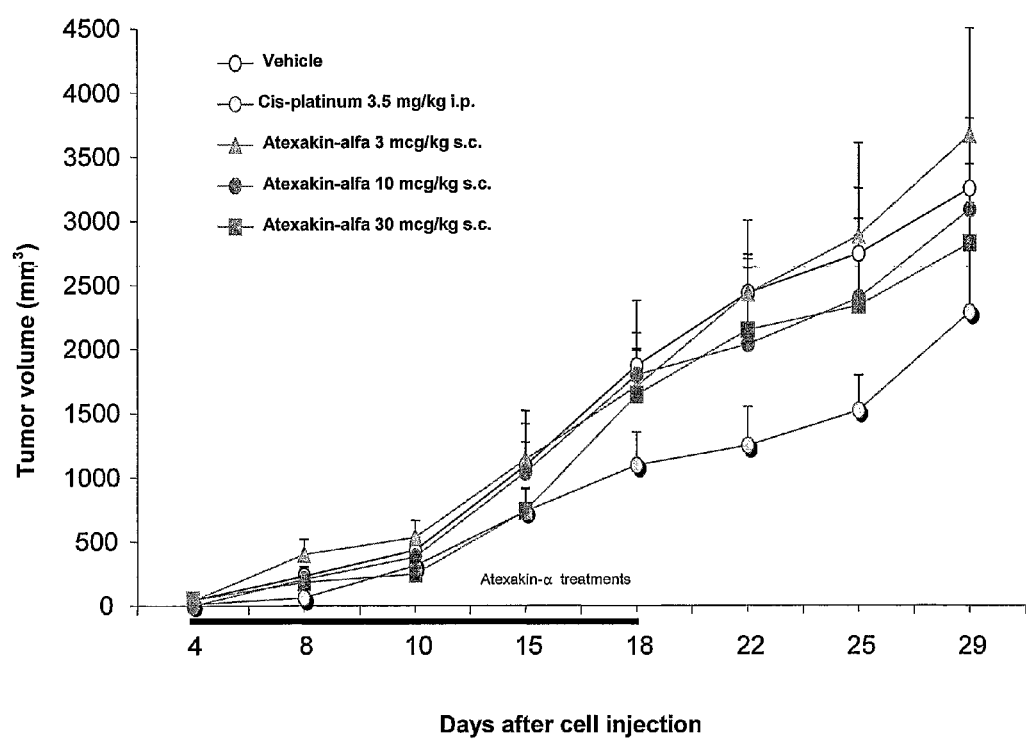

FIG. 32 shows the effect of IL-6 (atexakin alfa) on human WiDr colon carcinoma tumor growth in nude mice.

Figure 33:
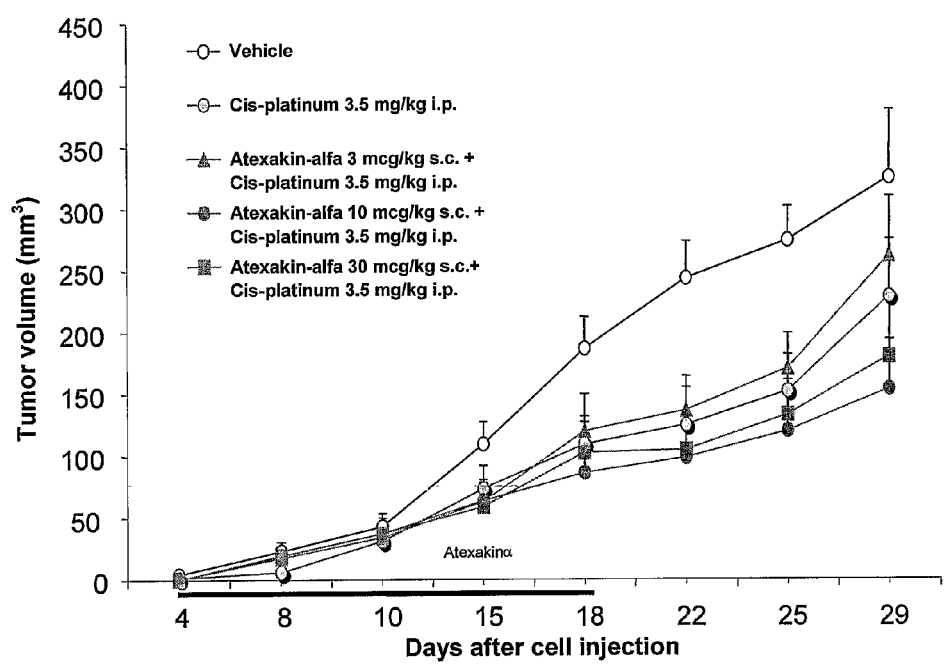

FIG. 33 shows the effect of IL-6 (atexakin alfa) in combination with cis-platinum on human WiDr colon carcinoma tumor growth in nude mice.

DETAILED DESCRIPTION OF THE INVENTION

The present invention relates to the use of a low dose of IL-6, or a mutein, isoform, fused protein, functional derivative, active fraction or circularly permutated derivative or a salt thereof, for the manufacture of a medicament for the treatment and/or prevention of chemotherapy-induced peripheral neuropathy (CIPN).

Currently, treatment of peripheral neuropathy is symptomatic and has no beneficial effect underlying damage to the nerves. Typically, CIPN is alleviated by dose reduction, which may compromise the efficacy of treatment.

Thus, the present invention presents a substantial progress, namely, the use of a low dose of IL-6, to prevent CIPN development and/or once CIPN is established, to treat and/or ameliorate CIPN-without impairing chemotherapeutic activity of the drugs. Moreover, according to the invention, administrating low doses of IL-6, will enable increasing the chemotherapeutic dose and/or to prolong chemotherapy when needed. For example the invention will allow administration of higher concentration of chemotherapy and/or more chemotherapy cycles than the concentration and number of cycles currently used when needed e.g. to combat more resistant and/or aggressive tumors.

Therefore the invention relates to the treatment and/or prevention of CIPN by a wide range of chemotherapy agents selected from vinca-alkaloids (e.g. vincristine and vinblastine), platinum-based compounds (e.g. cisplatin) and taxanes (paclitaxel and docetaxel), carboplatin or a combination of more than one agent thereof such as carboplatin and placitaxel, by administration of low dose of IL-6.

The invention is based on the findings that administrating low doses of IL-6 in reliable animal models is efficient in preventing CIPN as well as treating and/or ameliorating CIPN once the neuropathy is established.

For example, experiments carried out in animal models of CIPN showed that co-administration of IL-6 with the chemotherapic agent prevented chemotherapy-induced motor/sensory defects, and nerve degeneration. The protocols used show that IL-6 administration protected against chemotherapy-induced neuropathy regardless of the schedule of administration, namely, a dosage characterized by a IL-6 administration of three times per week, vis-à-vis daily administration, did not lead to a decrease of the neuro-protective effect of the compound.

In addition, experiments carried out in animal models in which neuropathy is already established, showed that IL-6 efficiently treated and/or ameliorated chemotherapy-induced sensory defects, loss of fiber/nerve function, reversed myelin sheath thinning, increased the ratio large/small fibers, and reduced the proportion of degenerated fibers induced by chemotherapy-treatment.

It should be noted that the active dose of human IL-6 as thrombopoietic factor in rodents is above 500 µg/kg, versus 10 µg/kg in monkeys (Herodin et al. 1992 Blood 80 (3) 688). Therefore human IL-6 appears to be 50 times more effective in primates than in rodents. Therefore human recombinant IL-6 (hr IL-6) is expected to be 50 times, or one order of magnitude more effective or at least 5 folds more effective in humans than in rodents. Since in the present embodiments, positives results in CIPN were found in rodents at doses in the range of 0.3 to 10 µg/kg, and very effective results were found at the doses of 3 and 10 µg/kg, thus a dose of 50, 10 and/or 5 time less human recombinant IL-6 is expected to be effective for preventing/treating CIPN in man. Preferable doses in human are in the range of about 0.06 up to 3 µg/kg, more preferably in the range of 0.1 to 2 µg/kg and more preferable at doses of about 0.2, 0.3, 1, 2, and up to 3 µg/kg.

Alternatively, a fixed low dose of IL-6 can be administrated regardless of the weight of the patient, such as low doses in the range of 4 up to 210 µg per patient, and preferably in the range of 7 to 140 µg and more preferable of about 4, 7, 14, 28, 70 or 140 µg IL-6 per patient.

Altogether, the results obtained unequivocally demonstrate the preventive or prophylactic and/or therapeutic value of a low dose of IL-6 in CIPN. The results obtained also showed that a low dose of IL-6 protected more efficiently than 4-MC from chemotherapy-induced neuropathy.

The terms "treating/ameliorating" used herein should be understood as preventing, inhibiting, attenuating, ameliorating or reversing one or more symptoms or cause(s) of chemotherapy neuropathy, as well as symptoms, diseases or complications accompanying chemotherapy-induced neuropathy. When "treating/ameliorating" chemotherapy-induced neuropathy, the substances according to the invention are given after onset of the disease, "prevention" relates to administration of the substances before any signs of disease can be noted in the patient.

Preventive administration is especially useful in patients having high-risk to be ill or suffer from CIPN, such as those patients having suffered from diabetes mellitus already for a prolonged period of time, patients who already have neuropathic symptoms due to acquired immune-deficiency syndrome (AIDS) and, patients with hereditary neuropathies or subjected to early treatment with neurotoxic chemotherapy etc.

IL-6 administration is especially useful in a patient exhibiting high levels of IL-6 receptor in the circulation.

The term "chemotherapy" relates to the treatment with drugs that kill cancer cells or make them less active The term "chemotherapy-induced neuropathy" relates to any form of chemotherapy-induced, or to one or more symptom (s) or disorder (s) accompanying or caused by chemotherapy, or complications of chemotherapy affecting nerves as described in detail in the introduction above.

The substance of the invention, IL-6, or a mutein, isoform, fused protein, functional derivative, active fraction or circularly permutated derivative or a salt thereof (the "substance"), can be used or administered in peripheral neuropathy caused by a variety of chemotherapeutic agents such as cisplatin, dicarbazine, streptozocin, cyclophosphamide, carmustine, lomustine, procarbazine, mitomycin, cytarabine, methotrexate, 5-fluorouracil, vinblastine, vincristine, bleomycin, paclitaxel, asparaginase, busulfan, carboplatin, dacarbazine, fludarabine, hydroxyurea, ifosfamide, mercaptopurine, mitotane, streptozocin, taxol and or a mixture of two or more agents thereof.

In one embodiment of the invention IL-6, or a mutein, isoform, fused protein, functional derivative, active fraction or circularly permutated derivative or a salt thereof, is used to treat and/or protect from CIPN when the chemotherapeutic agent is taxol, cisplatin and vincristine and or a combination such as a mixture of carboplatin and paclitaxel.

Taxol can be administered for example at a range of about 20-250 mg/m2, cisplatinum at a range of about 30-100 mg/m2, vincristine at a range of about 0.5-2 mg/m2 and carboplatin/placitaxel can be used at the range of 100 to 200 µg/m2 and preferably at about 175 µg/m2. Chemotherapy may be given in cycles of 1 and up to about 6 cycles, which may be separated by 3-4 weeks without chemotherapy administration. Chemo regimens can be found in WWW.ohaci.com/palm/chemopage.htm Oncology/hematology associates of central Illinois.

The substance of the invention can be administered according to the invention in a dose range of about 0.06 up to 3 µg/kg, more preferably in the range of 0.1 to 2 µg/kg and most preferable at doses of about 0.2, 0.3, 1, 2, and up to 3 µg/kg.

Alternatively low dose of IL-6 can be administrated regardless of the weight for example low doses are administered in the range of 7 to 140 µg per patient, and preferably of about 7, 28, 70 or 140 µg IL-6 per patient.

The substance of the invention may be either glycosylated at one or more sites, or non-glycosylated.

The substance of the invention can be a functional derivative comprising at least one chemical moiety attached to one or more functional groups, which occur as one or more side chains on the amino acid residues, and more preferably the moiety is a polyethylene glycol moiety.

The substance in accordance to invention may administered as a cell expressing the substance of the invention and/or as a vector, preferably a lentiviral vector, comprising the coding sequence of the substance of the invention.

A vector for inducing and/or enhancing the endogenous production of IL-6, in a cell normally silent for expression of a IL-6, or expressing amounts of IL-6 which are not sufficient, is also contemplated according to the invention. The vector may comprise regulatory sequences functional in the cells desired to express the IL-6. Such regulatory sequences comprise promoters or enhancers. The regulatory sequence is then introduced into the right locus of the genome by homologous recombination, thus operably linking the regulatory sequence with the gene, the expression of which is required to be induced or enhanced. The technology is usually referred to as "endogenous gene activation" (EGA), and it is described e.g. in WO 91/09955.

The invention relates also to methods for treating and/or preventing CIPN, comprising administering to a patient in need thereof a low dose of IL-6, or a mutein, isoform, fused protein, functional derivative, active fraction, circularly permutated derivative or a salt thereof, optionally together with a pharmaceutically acceptable carrier.

The invention also provides a method to treat CIPN high risk patients such as those patients having suffered from diabetes mellitus already for a prolonged period of time, patients who already have neuropathic symptoms due to diabetes mellitus, patients who already have neuropathic symptoms due to AIDS and, patients with hereditary neuropathies or subjected to early treatment with neurotoxic chemotherapy etc.

The invention also provides a method to treat and/or prevent CIPN in cancer patients, such as patients suffering of leukemia, cancer of the ovary or breast cancer, having elevated IL-6R level in the circulation.

The dose of the substance of the invention may be administered daily and preferably three times per week for at least two weeks.

The term "dose" relates to the quantity to be administered at one time, such as a specified amount of medication.

As used herein the term "muteins" refers to analogs of an IL-6, in which one or more of the amino acid residues of the naturally occurring components of IL-6 are replaced by different amino acid residues, or are deleted, or one or more amino acid residues are added to the original sequence of an IL-6, without changing considerably the activity of the resulting products as compared with the original IL-6. These muteins are prepared by known synthesis and/or by site-directed mutagenesis techniques, or any other known technique suitable therefore.

Muteins used in accordance with the present invention include proteins encoded by a nucleic acid, such as DNA or RNA, which hybridizes to DNA or RNA, which encodes an IL-6, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of an IL-6, such as to have substantially similar, or even better, activity to IL-6.

Characteristic activity of IL-6 is the capability of binding to the gp80 portion of the IL-6 receptor and/or capability of inducing hepatocyte proliferation. As long as the mutein has substantial capability of binding to the gp80 portion of the IL-6 receptor and/or capability of inducing hepatocyte proliferation, it can be considered to have substantially similar activity to IL-6. Thus, it can be determined whether any given mutein has at least substantially the same activity as IL-6 by means of routine experimentation comprising subjecting hepatocytes to such mutein, and to determine whether or not it induces hepatocyte proliferation e.g. by measuring BrdU or labelled methionine uptake or just by counting the cells the cells vis-à-vis non treated control cells and cells treated with WT IL-6. An Enzyme Linked ImmunoSorbent Assay (ELISA) type assay for measuring the binding of IL-6R/IL-6 chimera to gp130 has been described in detail in example 7 on page 39 of WO 99/02552, which is fully incorporated by reference herein. As long as the mutant has substantial binding activity to its binding region of GP80 it can be considered to have substantially similar activity to IL-6.

For example, a microtiter 96-well plate (Nunc) is coated with anti-human gp80 monoclonal antibody and 50 ng/ml of gp80 (both from R & D Systems, Minneapolis) is added. After washing in phosphate buffered saline, the IL-6 is added in different wells at different concentrations ranging from 0.1 to 50 ng/ml. After incubation overnight at 40 C, a rabbit polyclonal anti-IL-6 is added, followed by goat antirabbit Ig conjugated with horseradish peroxidase, which is detected by colored reaction (Sigma, St. Louis).

Thus it can be determined whether any given mutant has at least substantially the same activity as IL-6 by means of routine experimentation comprising subjecting such mutant e.g. to a simple sandwich binding assay to determine whether or not it binds to an immobilized gp80 or soluble gp80 (extracellular fragment of gp80) as described in example 7 of WO 99/02552.

In a preferred embodiment, any such mutein has at least 40% identity or homology with the sequence of mature IL-6. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990; Pearson 1988).

Muteins of IL-6, which can be used in accordance with the present invention, or nucleic acid coding thereof, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of IL-6 may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table A. More preferably, the synonymous amino acid groups are those defined in Table B; and most preferably the synonymous amino acid groups are those defined in Table C.

TABLE A

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE B

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE C

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IL-6 polypeptides, for use in the present invention include any known method steps, such as presented in U.S. Pat. Nos. 4,959,314, 4,588,585 and 4,737,462, to Mark et al; 5,116,943 to Koths et al., 4,965,195 to Namen et al; 4,879,111 to Chong et al; and 5,017,691 to Lee et al; and lysine substituted proteins presented in U.S. Pat. No. 4,904,584 (Shaw et al).

Specific muteins of IL-6, which are useful in connection with the present invention, have been described (WO9403492A1). Furthermore, EP667872B1 describes mutant IL-6 with improved biological activity over wild type IL-6. In addition to this, EP0656117 describes methods to isolate superagonists of IL-6. The mutants or superagonists may be used according to the invention.

The term "fused protein" refers to a polypeptide comprising an IL-6, or a mutein or fragment thereof, fused with another protein, which, e.g., has an extended residence time in body fluids. An IL-6 may thus be fused to e.g., an immunoglobulin or a fragment thereof.

"Functional derivatives" as used herein cover derivatives of IL-6, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-6, and do not confer toxic properties on compositions containing it.

These derivatives may, for example, include polyethylene glycol side-chains, which may mask antigenic sites and extend the residence of an IL-6 in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

An "active fraction" according to the present invention may e.g. be a fragment of IL-6. The term fragment refers to any subset of the molecule, that is, a shorter peptide that retains the desired biological activity. Fragments may be readily prepared by removing amino acids from either end of the IL-6 molecule and testing the resultant fragment for its properties to bind to gp80 and/or gp130. Proteases for removing one amino acid at a time from either the N-terminal or the C-terminal of a polypeptide are known, and so determining fragments, which retain the desired biological activity, involves only routine experimentation.

As active fractions of an IL-6, muteins and fused proteins thereof, the present invention further covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to IL-6 e.g. bind to the IL-6 binding site of gp80 and/or to gp130.

The term "salts" herein refers to both salts of carboxyl groups and to acid addition salts of amino groups of the IL-6 molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of IL-6 e.g. the ability to bind the IL-6 binding site of gp80 and or gp130.

"Isoforms" of IL-6 are proteins capable of binding gp80 and/or gp130 or fragment thereof, which may be produced by alternative splicing.

The term "circularly permuted derivatives" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The preparation of circularly permutated derivatives is described in WO95/27732.

In one embodiment of the invention, the substance of the invention is glycosylated at one or more sites.

The IL-6 according to the invention may be produced in any adequate eukaryotic or procaryotic cell type, like yeast cells, insect cells, bacteria, and the like. In one embodiment, IL-6 is produced in mammalian cells, such as in genetically engineered CHO cells as described in WO 99/02552.

In a further embodiment of the invention, the substance of the invention is not glycosylated. Advantageously, the molecule can then be produced in bacterial cells, which are not capable of synthesizing glycosyl residues, but usually have a high yield of produced recombinant protein. The production of non-glycosylated IL-6 has been described in detail in EP504751B1, for example.

In yet a further embodiment, the substance according to the invention comprises an immunoglobulin fusion, i.e. the molecules according to the invention are fused to all or a portion of an immunoglobulin. Methods for making immunoglobulin fusion proteins are well known in the art, such as the ones described in WO 01/03737, for example. The person skilled in the art will understand that the resulting fusion protein of the invention retains the biological activity of the IL-6. The resulting fusion protein ideally has improved properties, such as an extended residence time in body fluids (half-life), increased specific activity, increased expression level, or facilitated purification of the fusion protein.

Preferably, the substance according to the invention is fused to the constant region of an Ig molecule. It may be fused to heavy chain regions, like the CH2 and CH3 domains of human IgG1, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may be monomeric or multimeric, hetero- or homomultimeric.

Functional derivatives of the substance according to the invention may be conjugated to polymers in order to improve the properties of the protein, such as the stability, half-life, bioavailability, tolerance by the human body, or immunogenicity.

Therefore, a preferred embodiment of the invention relates to a functional derivative of the substance according to the invention comprising at least one moiety attached to one or more functional groups, which occur as one or more side chains on the amino acid residues.

A highly preferred embodiment relates to a substance of the invention linked to polyethlyenglycol (PEG). PEGylation may be carried out by known methods, such as the ones described in WO 92/13095, for example.

In one embodiment, the substance of the invention is administered in a dose ranging from 0.06 to 3 µg/kg body weight. In a preferred embodiment of the invention the substance is administered daily. In a further preferred embodiment, the substance is administered three times per week. In yet a further preferred embodiment, the substance is administered once a week.

The definition of "pharmaceutically acceptable" is meant to encompass any carrier, which does not interfere with effectiveness of the biological activity of the active ingredient and that is not toxic to the host to which it is administered. For example, for parenteral administration, the substance may be formulated in a unit dosage form for injection in vehicles such as saline, dextrose solution, serum albumin and Ringer's solution.

In one embodiment, the invention provides a pharmaceutical composition comprising a combination of IL-6, or an isoform, mutein, fused protein, functional derivative or fragment thereof, and one or more chemotherapic agent.

The substance can be administered to a patient in need thereof in a variety of ways. The routes of administration include intraliver, intradermal, transdermal (e.g. in slow release formulations), intramuscular, intraperitoneal, intravenous, subcutaneous, oral, epidural, topical, and intranasal routes. Any other therapeutically efficacious route of administration can be used, for example absorption through epithelial or endothelial tissues or by gene therapy wherein a DNA molecule encoding the IL-6 is administered to the patient (e.g. via a vector), which causes the IL-6 to be expressed and secreted in vivo. In addition the substance can be administered together with other components of biologically active agents such as pharmaceutically acceptable surfactants, excipients, carriers, diluents and vehicles.

For parenteral (e.g. intravenous, subcutaneous, intramuscular) administration, IL-6 can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

It is a further object of the present invention to provide for a method for treating and/or preventing CIPN, comprising administering to a patient in need thereof a low dose of IL-6, a mutein, fused protein, functional derivative, active fraction, circularly permutated derivative or salt thereof optionally together with a pharmaceutically acceptable carrier.

The dosage administered, as single or multiple doses, to an individual will vary depending upon a variety of factor, including the substance pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled.

The term "dosage" relates to the determination and regulation of the frequency and number of doses.

The invention relates to the use of a low dose of IL-6 or a mutein, fused protein, active fraction or circularly permutated derivative in the manufacture of a medicament for the treatment/prevention of CIPN.

The low dose of the substance can be administered before during and/or after chemotherapy. The low dose of the substance can be administered prophylacticaly before CIPN is established or for treating established CIPN.

The invention relates also to a kit comprising: one or more containers comprising each a chemotherapeutic agent; one container comprising IL-6 or a mutein, isoform, fused protein, functional derivative, active fraction or circularly permutated derivative or a salt thereof; and instructions for administration of said chemotherapeutic agent and said IL-6 for the prevention and/or treatment of chemotherapy-induced peripheral neuropathy.

Said kit may contain two containers comprising each a chemotherapeutic agent, for example one container may comprise carboplatin and another taxol.

The amount of IL-6, or a mutein, isoform, fused protein, functional derivative, active fraction or circularly permutated derivative or a salt thereof, in each container may be in the range of 4 to 210 µg, of 7 to 140 µg or about 4, 7, 14, 28, 70 or 140 µg.

The invention contemplates said kit further comprising a container with a neuroprotective drug such as neural growth factor (NGF) and glutamine.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

The present invention will now be described in more detail in the following non-limiting examples and the accompanying drawings.

EXAMPLES

Example 1

Vincristine Induced Neuropathy, Animals and Drug Administration

Vincristine induced neuropathy is a mixed type neuropathy (i.e. sensory and motor related neuropathy). Boyle and co-workers (Boyle et al., J Pharmacol Exp Ther. 1996 October; 279(1): 410-5) have developed a rat model of vincristine neuropathy, where sensory and motor peripheral defects as measured by behavioral tests (tail-flick and rotarod performance, respectively) has been reported to more closely resemble the condition in humans than any previously described. This model of vincristine-induced neuropathy was employed in order to explore whether IL-6 can protect from vincristine-induced neuropathy.

The experiments were carried out employing 10 weeks-old female Dark Agouti rats (Janvier, Le Genest-St-Isle, France). The rats were randomly distributed in 7 experimental groups as follows: (a) a vehicle control group receiving IP injection of 0.02% BSA in saline (n=10); (b) a vincristine-treated group (n=10) daily administered with sub coetaneous (SC) injection of 0.02% BSA in saline (see below); (c) four different groups of vincristine-treated rats, daily administered with SC injections of human recombinant IL-6 (Example 23) at the doses of 0.3, 1, 3, or 10 µg/kg (n=10 for each group); and (d) a vincristine-treated group receiving a daily intra peritoneal (IP) injection of 4-methylcatechol (4-MC). 4-MC is a standard compound with an established neuroprotective action, used at the dose of 10 µg/kg (n=10).

Animals were housed 2 per cage and maintained in a room with controlled temperature (21-22° C.) and a reversed light-dark cycle (12 h/12 h) with food and water available ad libitum.

Vincristine (Tocris, Illkirch, France) was administered by an injection of a vincristine solution from day 0 to 5, from day 8 to 12 and from day 15 to 16 at a dose of 0.15 mg/kg. A vincristine solution (0.03 mg/ml) was prepared in saline.

IL-6 was diluted in saline containing 0.02% BSA and was administered via subcutanuous route every day from the first day of vincristine administration until the end of the experiment.

4-MC (see previous page), was diluted in saline and injected daily via IP route from the first day of vincristine administration until the end of the study.

Figure 1:
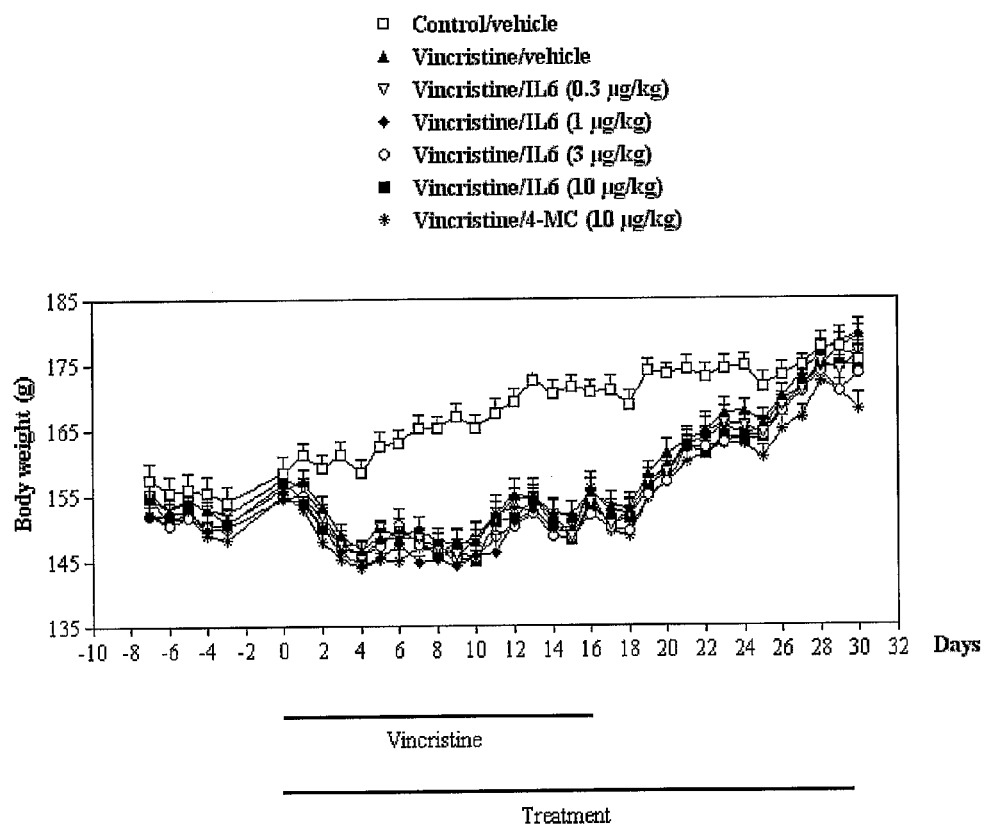
FIG. 1 shows the effect of vincristine, vincristine-IL-6 co-administration at the indicated doses or vincristine-4-MC co-administration on body weight of rats. Mean±s.e.m

The effect of vincristine on body weight was explored. FIG. 1 shows that animals treated with vincristine exhibit a significantly lower body weight than the control group [$F_{(6, 210)}=7.144$ and $p<0.001$; repeated measures ANOVA]. For example, vincristine intoxicated animals treated with vehicle lost about 10% of their weight at the completion of vincristine administration. However, no significant difference was detected between the groups that were subjected to vincristine treatment, regardless of IL-6 administration. Once vincristine was discontinued, the animals grew up rapidly.

Example 2

Effect of IL-6 Co-Administration in Preventing/Reducing Vincristine Mediated Motor Coordination Impairment In order to assess impairing of motor coordination by vincristine and the effect of IL-6 co-administration, a vehicle control group of rats receiving IP injection of 0.02% BSA in saline (n=10); (b) a vincristine-treated group (n=10) treated daily with SC injection of 0.02% BSA in saline (Example 1); (c) four different groups of vincristine-treated rats (see below) daily administered with SC injections of IL-6 at the doses of 0.3, 1, 3, or 10 µg/kg (n=10 for each group); and (d) a vincristine-treated group daily administered with IP injection of 4-MC, at the dose of 10 µg/kg (n=10), were monitored in a walking test (Example 16).

Figure 2:
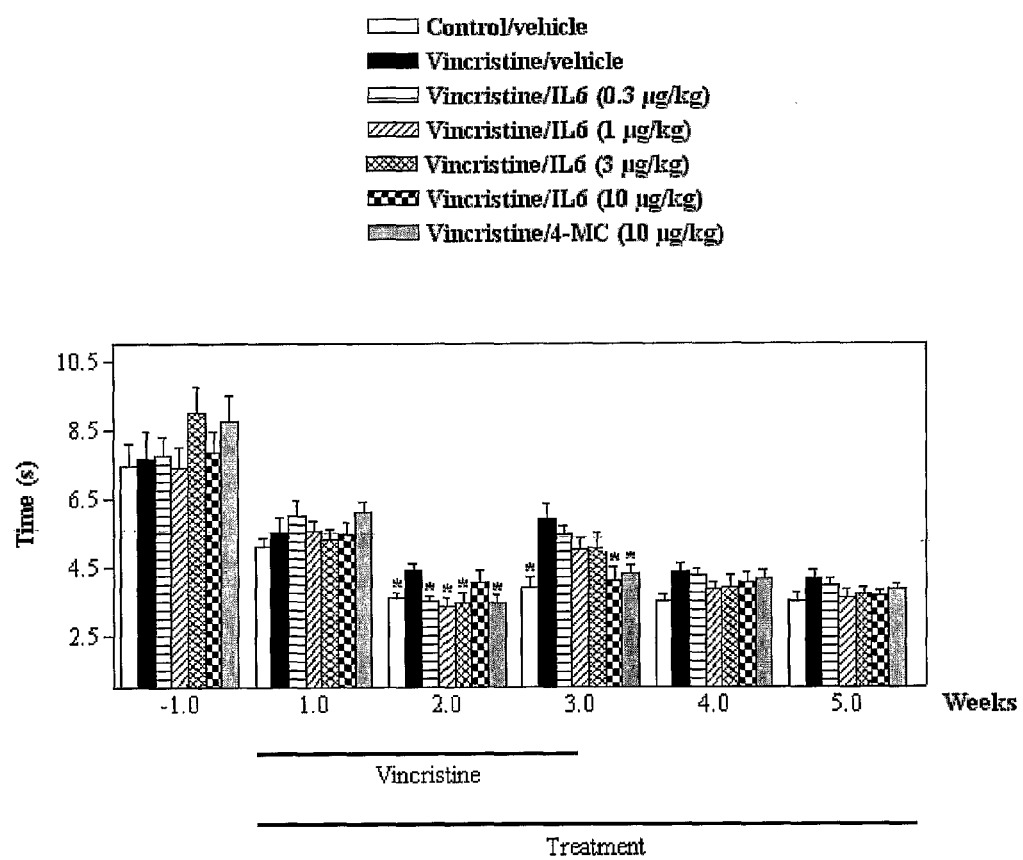
FIG. 2 shows prophylactic effect of IL-6 on vincristine-mediated neuropathy manifested by prevention of vincristine-induced motor coordination loss. The Figure shows results of walking tests in vincristine-treated versus vincristine-IL-6 co-administrated at the indicated doses, or vincristine-4-MC co-administrated rats.

FIG. 2 summarizes the walking test results in control, vincristine-treated and IL-6 treated animal groups. The results show the time required to each experimental animal group to traverse the rod.

After 2 and 3 weeks of vincristine administration, the performance was significantly reduced, compared to non-treated controls rats.

Rats co-administrated with IL-6, traversed the rod faster compared with rats administered with vincristine alone. The beneficial effect of IL-6 was observed with all of the doses of IL-6 tested, 0.3, 1, 3, or 10 µg/kg was observed 2 and three weeks after intoxication.

Therefore the results obtained in walking tests demonstrate that co-administration of IL-6, at all the IL-6 doses tested, 0.3, 1, 3, or 10 µg/kg, prevents motor coordination impairment induced by vincristine.

Example 3

Effect of IL-6 In Vincristine-Induced Nociception Loss

In order to evaluate sensory defects (i.e. nociception loss) induced by vincristine in rats and the effect of IL-6 co-administration, a vehicle control group of rats receiving IP injection of 0.02% BSA in saline (n=10); (b) a vincristine-treated group (n=10) treated daily with SC injection of 0.02% BSA in saline (Example 1); (c) four different groups of vincristine-treated rats (see below) daily administered with SC injections of IL-6 at the doses of 0.3, 1, 3, or 10 µg/kg (n=10 for each group); and (d) a vincristine-treated group daily administered with IP injection of 4-MC, at the dose of 10 µg/kg (n=10), were monitored in a hot plate test as described in Example 15.

The results of the hot plate test are summarized in FIG. 3. In the vincristine-treated group a delayed first reaction to heat was observed compared to control non-treated group of rats. The delayed first reaction was significant 3 and 5 weeks after treatment initiation.

Co-administration of IL-6, at all the doses tested, significantly prevented nociception 5 weeks after treatment initiation, whilst some preventive tendencies of IL-6 could be observed throughout the experiment.

4-MC did not appear to have any major preventive effect on vincristine-induced nociception loss in rats.

Therefore the results obtained in hot test plate demonstrate that co-administration with IL-6, at all the doses tested, 0.3, 1, 3, or 10 µg/kg protected from vincristine-induced nociception loss in rats. The hot plate test demonstrated also that IL-6 confers better protection that 4-MC from vincristine-induced nociception loss in rats (FIG. 3).

Example 4

Electrophysiological Tests (Electromyography or EMG) Show Protective Effect of IL-6 Against Vincristine-Induced Neuropathy In parallel to behavioral tests, electrophysiological test as described in Example 17, were carried out to evaluate fiber/nerve function in vincristine-administered rats vis-à-vis rats co-administrated with IL-6.

A significant reduction in the M wave amplitude (tested as described in Example 17) could be already detected 2 weeks after vincristine administration (FIG. 4). The animals lost about 20% of amplitude compared to control untreated animals. Amplitude loss was maintained even after vincristine cessation.

Co-administration with IL-6, at all the IL-6 doses tested, was shown to prevent vincristine-induced loss of M wave amplitude and IL-6 employed at the dose of 1-10 µg/kg fully preserved the H wave amplitude.

Co-administration with 4-MC was observed to protect the loss of M wave amplitude only transiently, while protection by 3-10 µg/kg IL-6 was stable throughout the experiment.

As shown in FIG. 5, the first change in compound muscle action potential (CMAP) latency was detected only after cessation of vincristine treatment.

Vincristine-induced CMAP latency was shown to be reduced by co-administration of IL-6 ($p<0.05$; Dunnett's test) at all the concentrations tested 0.3-10 µg/kg. Rats co-administered with 10 µg/kg IL-6, fully preserved their CMAP latency time throughout the experiment.

An initial change in sensitive nerve conduction velocity (SNCV) was detected upon vincristine cessation (or of 2 weeks after vincristine administration initiation FIG. 6). At that time, a slight reduction in SNCV was observed compared to that in untreated control rats. The effect of vincristine became significant 5 weeks after vincristine treatment initiation, exhibiting a loss of about 10 m/s.

A full restoration of SNCV was observed in vincristine treated animal groups co-administered with 1-10 µg/kg IL-6.

Therefore, results of electrophysiological tests demonstrate that IL-6 co-administration, at all the IL-6 doses tested, 0.3, 1, 3 and 10 µg/kg, protected against vincristine-induced fiber/nerve function loss. Electrophysiological tests also demonstrated that IL-6 confers better protection that 4-MC against vincristine-induced fiber/nerve function loss (FIG. 4).

Example 5

Morphometric Analysis Show Protective Effect of IL-6 Against Vicristine-Induced Neuropathy Histomorphometric analyses were carried out as described in Example 18 at the completion of the experiments, to explore morphologic changes occurring in fiber and axon diameter and myelin thickness in rats treated with vincristine and in rats co-administrated with IL-6.

As shown in FIG. 7, sciatic nerves harvested from vincristine treated rats exhibited a significant decrease in fiber diameter compared to control non-treated specimens. Co-administration with IL-6 at the doses 1-10 µg/kg prevented vincristine-induced fiber shrinkage. Vincristine-induced fiber shrinkage was also protected by 4-MC treatment.

The diameter of the axons significantly decreases in vincristine treated rats (FIG. 8). Co-administration of IL-6 at doses of 0.3-10 µg/kg, significantly reduced/prevented the decrease in axon diameter by vincristine.

4-MC treatments significantly reduced/prevented the decrease in axon diameter by vincristine.

Myelin thickness was significantly reduced in axons from the vincristine-treated compared to control non-treated rats (FIG. 9).

Co-administration of IL-6 at doses of 1-10 µg/kg, reduced/prevented vincristine-induced myelin loss.

The percentage of degenerated fibers was also monitored in samples harvested from control, vincristine and vincristine-IL-6 administered rats (FIG. 10). The percentage of degenerated fibers collected from samples of vincristine treated rats was two times higher than that in samples from control rats. Moreover, the percentage of myelinated fibers in vincristine treated group was less than that in the control non-treated group.

Co-administration with IL-6 (0.3-10 µg/kg) or 4-MC was found to decreased the percentage of degenerated fibers in vincristine treated rats.

Thus, the above morphometric analysis demonstrate that co-administration with IL-6, at all the doses tested, 0.3, 1, 3 and 10 µg/kg, efficiently prevented/reduced vincristine-induced nerve degeneration and particularly prevented reduction in fiver and axon diameter, reduction in myelin thickness and degeneration of fibers.

A 5-10 mm diameter area of skin was punch-biopsied from the hindpaw. Skin samples were immediately fixed overnight in paraformaldehyde at 4° C., incubated (overnight) in 30% sucrose in 0.1 M PBS for cryoprotection, embedded in OCT and frozen at −80° C. until cryocut. 50 µm-thick cryosections were then cut vertical to the skin surface with a cryostat. Free-floating sections were incubated for 7 days in a bath of rabbit anti-protein gene product 9.5 (1:10000; Ultraclone, Isle of Man, UK) at 4° C. The sections were then processed to reveal immunoreactivity according to the ABC peroxidase method. Briefly, they were incubated in for 1 hr with biotinylated anti-goat antibody (1:200), then 30 min in the avidin biotinylated complex at room temperature. Peroxidase activity was visualized using DAB system. Sections were then counterstained with eosin or hematoxylin. Sections were dehydrated, cleared with bioclear and mounted on eukitt. The number of dermal nerves of 3 microscope fields was counted manually under 40 magnification view. Vincristine intoxication induced more than 50% decrease in the density of epidermal nerve fibers. Skin biopsy is among the various techniques to monitor neuropathy in human. The results of the present experiment indicate that vincristine intoxication was associated with a large decrease in the density of dermal fibers, resembling to that occurring in the clinical setting. Treatment with 10 µg/kg IL-6-fully prevented this phenomenon of dermal fiber loss (not shown).

Example 6

Cisplatin Induced Neuropathy, Animals and Drug Administration

A reliable animal model for cisplatin induced neuropathy, developed by Holmes and co-workers (Holmes et al., Toxicol Sci. 1998 December; 46(2): 342-51) was employed to explore the effect of IL-6 co-administration in cisplatin induced neuropathy. Cisplatin-induced neuropathy in rat has been described to mirror the clinical settings. Indeed, behavioral and electrophysiological correlate of axonal degeneration (as seen in human) has been reported previously in the rat model of cisplatin neuropathy (Holmes et al., 1998).

10 weeks-old female Dark Agouti rats (Janvier, Le Genest-St-Isle, France) were randomly distributed in 7 experimental groups as following: (a) a vehicle control group (n=10), injected with a sterile solution of saline-BSA 0.02% (weight/volume); (b) a cisplatin-intoxicated group (n=10) injected with a sterile solution of saline-BSA 0.02%; (c) 4 treated-cisplatin-intoxicated groups (n=10) consisting of animals receiving daily SC injections of IL-6 compound at 4 different doses: 0.3, 1, 3, 10 µg/kg; and (d) a 4-methylcatechol (4-MC)-treated, cisplatin-intoxicated group (n=10) receiving a daily IP injection of 4-MC at 10 µg/kg.

The rats were group-housed (2 animals per cage) and maintained in a room with controlled temperature (21-22° C.) and a reversed light-dark cycle (12 h/12 h) with food and water available ad libitum. All experiments were carried out in accordance with institutional guidelines.

Neuropathy was induced by intraperitoneal injection of cisplatin (Sigma, L'Isle d'Abeau Chesnes, France) twice a week at a dose of 2 mg/kg during 4 weeks. The drug was diluted in 0.9% sterile aqueous solution of sodium chloride.

IL-6 was diluted in a sterile solution of saline-BSA 0.02% and administered via subcutanuous route every day from the first day of cisplatin administration to the end of the experiment.

4-MC was diluted in 0.9% sterile aqueous solution of sodium chloride and injected daily via IP route since the first day of cisplatin administration.

The effect of cisplatin on weight body was explored. FIG. 11 shows that animals treated with cisplatin demonstrated a significantly lower body weight than the control group [p<0.001]. It was also noted that the cisplatin administration induced a marked inhibition of animal growth, regardless of IL-6 treatments undertaken. For example, cisplatin intoxicated animals treated with vehicle lost about 10% of their weight at the completion of cisplatin administration. Once the cisplatin was withdrawn, the animals grew up rapidly.

Example 7

Effect of IL-6 in Cisplatin Induced Nociception Loss

In order explore sensory defects induced by cisplatin treatments (i.e. nociception loss) and the effect of IL-6 co-administration, a vehicle control group receiving IP injection of 0.02% BSA in saline (n=10); (b) a cisplatin treated group (n=10) daily administered with SC injection of 0.02% BSA in saline (Example 1); (c) four different groups of cisplatin-treated rats (see below) daily administered with SC injections of IL-6 at the doses of 0.3, 1, 3, or 10 µg/kg (n=10 for each group); and (d) a cisplatin-treated group receiving a daily IP injection of 4-MC at the dose of 10 µg/kg (n=10), were monitored using a hot plate test as described in Example 15.

Three weeks after cisplatin administration, the rats exhibited a significant delayed first reaction to heat compared to control non-treated rats (FIG. 12). The delayed first reaction to heat in the cisplatin treated group versus the control group was significant and continued even after cessation of the cisplatin treatment (or 5 and 6 weeks after cisplatin treatment initiation).

Co-administration with IL-6 at all the doses tested, 0.3, 1, 3, or 10 µg/kg, overall prevented/reduced delay of the first reaction to heat by cisplatin ($p \leqq 0.05$).

The delay of the first reaction to heat by cisplatin was fully prevented by co-administration with 10 µg/kg IL-6.

The 4-MC treatment produced a slight but not significant decrease of the first reaction time in 3 weeks cisplatin-treated rats, compared to rats treated with cisplatin alone. The difference was significant only 4 and 6 weeks after cisplatin treatment initiation.

The results obtained in the hot plate tests demonstrate that co-administration of IL-6, with cisplatin prevented cisplatin-mediated sensory defects at all the doses tested, 0.3, 1, 3 and 10 µg/kg.

Example 8

Electrophysiological Tests (Electromyography or EMG) Show Protective Effect of IL-6 Against Cisplatin-Induced Neuropathy Electrophysiological monitoring in cisplatin-induced neuropathy model was carried out as described in Example 17. The objective was to assess the effect of co-administration with IL-6 in cisplatin-induced loss of fiber/nerve function.

The first change in the H wave amplitude was observed 3 weeks after cisplatin administration (FIG. 13). A slight reduction in amplitude was observed in the cisplatin treated group compared to the control non-treated group. At 4 to 6 weeks following cisplatin treatment initiation, the H wave amplitude was dramatically reduced by about 80%.

Whilst co-administration of each, 0.3, 1, 3 and 10 µg/kg, IL-6 was found to reduce/prevent the loss of H wave amplitude, co-administration with 10 µg/kg IL-6 fully prevented the loss of H wave amplitude throughout the experiment.

In contrast, 4-MC co-administration had only a delayed and transient effect in preventing the loss of H wave induced by cisplatin (FIG. 13).

The first alteration in sensitive nerve conduction velocity (SNCV) was observed 4 weeks after cisplatin administration. At that time, the signal velocity was significantly slow than in the corresponding non-treated control (FIG. 14).

Co-administration with IL-6 was found to improve SNCV, especially at 3 and 10 µg/kg IL-6 (FIG. 14) after 5 weeks.

Co-administration with 4-MC transiently prevented the decrease in SNCV of cispaltin intoxicated, only after 5 weeks of treatment (FIG. 14).

The results of the above electrophysiological tests demonstrate that co-administration with IL-6 efficiently prevents cisplatin-induced loss of fiber/nerve function. The results of the electrophysiological tests also show that IL-6 is more effective in preventing cisplatin-induced loss of fiber/nerve function than 4-MC (FIGS. 13 and 14).

Example 9

Protective Effect of IL-6 Against Cisplatin-Induced Neuropathy—A Morphometric Analysis Histomorphometric analyses were carried out at the completion of the experiment to explore morphologic changes occurring in fiber/axon diameter and myelin thickness following cisplatin administration and the effect of IL-6 co-administration.

FIG. 15 shows fiber diameter measurements in samples harvested from control, cisplatin and cisplatin IL-6 co-administered rats.

The resulting diameter measurements demonstrate that cisplatin significantly decreases fibers diameter. Results from specimen of rats co-administered with IL-6, at all the IL-6 doses tested, demonstrate that IL-6 prevents/reduce the diameter decrease by cisplatin. A significantly statistical difference was detected at the range of 1-10 µg/kg IL-6. Similarly, IL-6 co-administration prevents/reduces cisplatin-induced axon diameter decrease (FIG. 16). A statistically significant difference was detected at the range of 1-10 µg/kg IL-6.

In addition, measurements of percent of myelinated fibers was carried out in fibers harvested from control non-treated, cisplatin treated rats and cisplatin co-administered with IL-6 rats (FIG. 17). A significant reduction in the percent of myelinated fibers was observed in cisplatin treated rats compared to that in control non-treated rats.

It was found that IL-6 (1, 3, 10 µg/kg) significantly protected fibers against the loss of myelin wall.

4-MC treatment protected against the decrease in cisplatin-induced fiber diameter or axon and induced a significant protection against loss of myelin wall.

Also, the percentage of degenerated fibers was monitored in samples collected from control, cisplatin treated rats and rats co-administered with IL-6 and cisplatin (FIG. 18). The percentage of degenerated fibers in samples collected from cisplatin treated rats was found to be two-folds higher than that in samples collected from control non-treated rats. In addition to that, the percentage of myelinated fibers was reduced in the cisplatin treated group compared to that in the control non-treated group FIG. 17).

Co-administration with 1, 3, 10 µg/kg IL-6 was found to reduce the percentage of degenerated fibers by cisplatin (FIG. 18). FIG. 17 shows that in addition of reducing the percentage of degenerated fibers, co-administration with IL-6, increased myelinated fibers in cisplatin treated rats (FIG. 17).

Therefore, the above morphometric analysis demonstrated that co-administration of 1, 3 or 10 µg/kg IL-6, efficiently prevented/reduced nerve degeneration and particularly prevented the reduction of axon diameter, reduction of myelin thickness or loss of myelin wall and degeneration of fibers by cisplatin.

Example 10

Therapeutic Effect of IL-6 in Cisplatin-Induced Neuropathy Model—Animals and Drug Administration In the preceding experiments co-administration of IL-6 (0.3, 1, 3, 10 µg/kg) with chemotherapy was shown to prevent/reduce the neuropathic defects caused by chemotherapy in rats, as evidenced by behavioral, electrophysiological and histological assessments. In such experiments IL-6 therapy was initiated prior to or during development of neuropathy. Therefore in the previous experiments the prophylactic effect of IL-6 on the development of chemotherapy-related neuropathy was addressed. The following experiment was carried out to evaluate the effect of IL-6 after the neuropathy is already established in the animal model. The potential therapeutic effect of IL-6 was investigated using behavioral, electrophysiological and histological assessments.

10 weeks-old female Dark Agouti rats (Janvier, Le Genest-St-Isle, France) were randomly distributed in 5 experimental groups as following: (a) a vehicle control group (n=10), injected with a sterile solution of saline-BSA 0.02% (weight/volume); (b) a cisptatin-intoxicated group (n=10) injected with a sterile solution of saline-BSA 0.02%; (c) 2 treated-cisplatin-intoxicated groups (n=10) consisting of animals receiving daily SC injections of IL-6 compound at 2 different doses: 3 and 10 µg/kg; and (d) a 4-methylcatechol (4-MC)-treated, cisplatin-intoxicated group (n=10) receiving a daily IP injection of 4-MC at 10 µg/kg.

The rats were group-housed (2 animals per cage) and maintained in a room with controlled temperature (21-22° C.) and a reversed light-dark cycle (12 h/12 h) with food and water available ad libitum.

Neuropathy was induced by intraperitoneal injection of cisplatin (Sigma, L'Isle d'Abeau Chesnes, France) twice a week at a dose of 2 mg/kg during 4 weeks. The drug was diluted in 0.9% sterile aqueous solution of sodium chloride.

IL-6 was diluted in a sterile solution of saline-BSA 0.02% and administered via subcutanuous route every day from day 23 (last week of cisplatin administration) to the end of the experiment.

4-MC was diluted in 0.9% sterile aqueous solution of sodium chloride and injected daily via IP route from day 23 to the end of the experiment.

Body weight and survival rate were recorded every day.

Hot plate and EMG testing were performed on days –6, 23, 30, 37 and 44.

The first day of cisplatin administration was considered as day 1.

Example 11

Therapeutic Effect of IL-6 in Nociception Loss Established by Cisplatin

In order to check whether IL-6 may cure and/or ameliorate sensory defects (or nociception loss) induced by cisplatin, rats were treated with (a) a vehicle control group (n=10), injected with a sterile solution of saline-BSA 0.02% (weight/volume); (b) a cisplatin-intoxicated group (n=10) injected with a sterile solution of saline-BSA 0.02%; (c) 2 treated-cisplatin-intoxicated groups (n=10) consisting of animals receiving daily SC injections of IL-6 compound (Example 10) at 2 different doses: 3 and 10 µg/kg; and (d) a 4-methylcatechol (4-MC)-treated, cisplatin-intoxicated group (n=10) receiving a daily IP injection of 4-MC at 10 µg/kg, and tested using a hot plate test as described in Example 15.

The results show that from day 2 (baseline) to day 23, the hot plate score in control animals exhibited a marked decrease, a phenomenon associated with habituation to the test. From day 23 onwards, the score of control animals was stable.

During cisplatin administration and over the 3 weeks post-cisplatin treatment, cisplatin-treated group showed a significant delayed first reaction to heat compared to control non-treated rats (FIG. 19).

Two weeks after IL-6 treatment initiation, an overall reduction in the time of the first reaction was observed in rats treated with IL-6 ($p \leq 0.05$, Manova-Dunnett's test). Significant results with IL-6 were observed 2 weeks after IL-6 treatment with the dose of 10 µg/kg ($p \leq 0.05$, Anova-Dunnett's test).

Reduction of the time of the first reaction to heat in rats treated with 4-MC was observed also, after 2 weeks from 4-MC treatment initiation ($p \leq 0.05$, Anova-Dunnett's test).

The results obtained using the hot plate test show that IL-6 efficiently cured and/or ameliorate cisplatin-induced sensory defects.

Example 12

Therapeutic Effect of IL-6 in Cisplatin-Induced Neuropathy—Electrophysiological Measurements Electrophysiological tests described in Example 17, were carried out in parallel to the behavioral tests (described in the preceding example) in cisplatin-established neuropathy model. The objective was to assess the therapeutic effect of IL-6 in cisplatin-induced loss of fiber/nerve function.

In this set of experiments, the first change in the H wave amplitude was detected 23 days after cisplatin treatment initiation (FIG. 20). A dramatic loss in signal amplitude (about 70%) was observed in the cisplatin treated group. A spontaneous recovery of H-wave amplitude was not observed.

IL-6 treatment employing 3 and 10 µg/kg reversed the loss of H wave amplitude ($p \leq 0.05$, Manova-Dunnett's test). As early as 1 week after initiation of the IL-6 treatment, about 50% of the amplitude loss was recovered and by 2 weeks of IL-6 treatment full recovery occurred (FIG. 20).

4-MC treatment also reversed the cisplatin-induced H wave loss in amplitude.

The first alteration of sensitive nerve conduction velocity (SNCV) induced by cispaltin administration could be observed 23 days after initiation of cisplatin treatment (FIG. 21). SNCV in cisplatin treated rats was found to be significantly slower than SNCV in the corresponding untreated control group ($p \leq 0.01$, Manova-Dunnett's test) (FIG. 21).

The results show that IL-6 at a dose of 3 µg/kg, significantly ($p \leq 0.01$, Manova-Dunnett's test) improved the SNCV in cisplatin-treated animals, after only 1 week of treatment.

In contrast, 4-MC treatment appeared to improve SNCV of cispaltin treated rats, but a significant statistical difference was only detected 2 weeks after treatment initiation. ($p \leq 0.05$, Anova-Dunnett's test).

Therefore, the results of the electrophysiological tests demonstrate that a significant improvement in the SNCV in cisplatin-treated animals was observed after only 1 week of IL-6 treatment and the early effect was observed using the lowest dose of IL-6 tested, i.e. 3 µg/kg and reversed the loss of H wave. The electrophysiological tests demonstrate also that IL-6 is more efficient than 4-MC in curing and or ameliorating loss of fiber/nerve function induced by cisplatin (FIG. 21).

Example 13

Therapeutic Effect of IL-6 in Cisplatin-Induced Neuropathy—A Morphometric Analysis Histomorphometric analyses were carried out at the completion of the experiment to explore morphologic changes occurring in fiber and axon diameter and myelin thickness in the model of cisplatin induced CIPN and changes occurring after IL-6 administration in such model.

The results show that before therapy initiation (up to day 23), the overall size of myelin in cisplatin treated rats was slightly reduced as compared to the control non-treated rats but the difference was not significant (p>0.05, student t-test) (FIG. 22).

It was observed that samples collected from cisplatin treated rats contained a significant greater proportion of degenerated fibers than from control non-treated rats (FIG. 23A, p≦0.05, student t-test). In addition, the proportion of non-degenerated myelinated fibers was lower in cisplatin treated group than in control non-treated group (FIG. 23B).

A slight but not significant reduction in myelin area was observed 44 days after cisplatin treatment initiation (p>0.05, One-way Anova) (FIG. 24).

Administration of IL-6 at 10 μg/kg appeared to reverse cisplatin-induced myelin sheath thinning.

In contrast, 4-MC treatment did not interfere with cisplatin-induced myelin sheath thinning.

Small (diameter <8 μm) and large (diameter ≧8.5 μm) fibers were monitored and the ratio large/small fiber was calculated. The results in FIG. 25 show that the ratio large/small fiber was markedly reduced in samples harvested from cisplatin-treated rats. A slight increase in the large/small fibers ratio was observed after IL-6 treatment.

As illustrated in FIG. 26A, 3 weeks after the cessation of cisplatin administration, the proportion of degenerated fibers was still significantly higher in cisplatin treated compared to controls non-treated samples (p≦0.05, Dunnett's test). Moreover, the proportion of non-degenerated myelinated fibers was lower in cisplatin treated group than in control group (FIG. 26B). Treatment of the rats with IL-6 significantly reduced the percentage of degenerated fibers. A significant effect was obtained with 10 μg/kg IL-6.

In contrast, a slight but not significant reduction on the proportion of degenerated fibers was induced by 4-MC treatment (p>0.05, Dunnett's test).

The above morphogenic analysis results, demonstrate that IL-6 at 10 μg/kg reverses myelin sheath thinning and degeneration of fibers. The morphogenic analysis shows that IL-6 is more efficient than 4-MC in restoring myelin and fiber degeneration mediated by cisplatin (FIGS. 24 and 26).

Altogether, the behavioral tests in Example 11, the electrophysiological tests in Example 12 and the present morphogenic analysis unequivocally demonstrate the therapeutic value of low doses of IL-6 in cisplatin induced neuropathy. The tests also show that low doses of IL-6 have a better therapeutical effect than 4-MC against cisplatin-induced neuropathy.

Example 14

Effect of IL-6 Co-Administration in Taxol Induced Neuropathy

Previous examples show the effect of IL-6 in neuropathies induced by cisplatin or vincristine.

The aim of the following experiment was to investigate the potential neuroprotective effect of IL6 in an additional model of chemotherapeutic induced neuropathy mediated by taxol. The potential preventive effect of IL-6 co-administration was tested. Administration of IL-6 was initiated together with taxol administration. The doses of IL-6 of 3 and 10 μg/kg were administered daily or in the case 10 μg/kg also only 3 times per week.

Females 10 weeks old aged Dark Agouti rats were used, 12 animals per group were included as following
1. Vehicle daily sc
2. Taxol Vehicle daily sc, day 1 to day 49
3. Taxol IL-6 3 μg/kg daily, sc day 1 to day 49
4. Taxol IL-6 10 μg/kg daily, sc day 1 to day 49
5. Taxol IL-6 10 μg/kg, sc 3×/wk (TIW) day 1 to day 49
6. 4-MC 10 μg/kg daily, (intraperotoneal) i.p. day 1 to day 49

The taxol was diluted in a solution of cremophor/ethanol/dextrose 5% and administered twice a week during 4 weeks.

4-MC and test compounds treatment was initiated the first day of intoxication and was stopped at the end of the study.

The study was performed on 8 weeks (1 week for the baseline, 4 weeks for the taxol intoxication and 3 weeks of recovery).

Control, taxol, and taxol-IL-6 co-administered group of rats at the indicated doses were subjected to electrophysiological monitoring to assess the effect of IL-6 in taxol-induced loss of fiber/nerve function.

H wave latency was monitored in all groups of rats. A significant increase in H wave latency was observed 3 weeks after taxol treatment. The time of latency dramatically increased 6 weeks after taxol treatment.

Co-administration of IL-6, either 3 or 10 μg/kg daily or 3 times per week was found to prevent/reduce H wave latency throughout the experiment (FIG. 27).

4-MC treatment showed an improvement in H wave latency in weeks 3, 5, 6 and 7.

H-wave amplitudes were monitored in samples from group of rats treated with taxol and taxol rats administered with IL-6 or 4-MC. It was found that IL-6 at all the dosages tested significantly prevented the reduction in H wave amplitude induction by taxol throughout the experiment. In contrast, the prevention of H-wave amplitude reduction by 4-MC was not significant throughout the experiment (FIG. 28).

The first alteration in sensitive nerve conduction velocity (SNCV) induced by taxol administration was observed 3 weeks after cisplatin administration. At that time, the signal velocity was significantly slower than that of the corresponding velocity in non-treated control (FIG. 29).

The co-administration of IL-6, either 3 or 10 μg/kg daily or 3 times per week, with taxol was found to prevent alterations in SNCV by taxol.

The results demonstrate that co-administration of IL-6, at all doses either daily or 3 times per week, effectively prevents taxol-induced loss of fiber/nerve function. The results also demonstrate that the beneficial preventive effects of low doses of IL-6 co-administration are more significant than those of 4-MC co-administration (FIG. 28).

Example 15

Sensory Function-Hot Plate Test

The rat was placed inside a glass cylinder of 17 cm height and 21 cm diameter on a heating-plate maintained at 52° C. (Medite OTS 40, Microm, Francheville, Rhône, France). The animal behavior was observed, particularly the licking of a foot and the adjusted leap. The latency before licking a foot or before jumping to escape the heat (adjusted leap) was recorded. The time needed to feel the thermal pain is related to the thermal sensitivity and tends to increase when thermal sensitivity is altered.

Example 16

Motor Coordination Test

The motor coordination was assessed using walking test, which consists at measuring the time taken by a rat placed at one extremity of a 100 cm-long horizontal wooden rod of 5.5 cm diameter, 40 cm above the table, to cover a distance of 1 m on this rod. Three tests (maximum duration: 60 s each) were performed, and the mean value was calculated and retained as characteristic value. If the animal fell down, it was scored with a maximum of 60 s.

Example 17

Electromyography (EMG)

Electrophysiological recordings were performed using a Neuromatic 2000M electromyograph (EMG) (Dantec, Les Ulis, France). Rats were anaesthetized by IP injection of 60 mg/kg ketamine chlorhydrate (Imalgene 500®, Rhône Merieux, Lyon, France). The normal body temperature was maintained around 30° C. with a heating lamp and verified using a contact thermometer (Quick, Bioblock Scientific, Illkirch, France) placed on the tail surface.

Compound muscle action potential (CMAP) of M wave signal (or electrically evoked muscle potential) was recorded in the gastrocnemius muscle after stimulation of the sciatic nerve. M wave reflects the current developed during the action potential of muscle fibers. A reference electrode and an active needle were placed in the hind paw. A ground needle was inserted on the lower back of the rat. Sciatic nerve was stimulated with a single 0.2 ms pulse at supramaximal intensity. The velocity of the motor wave was recorded and expressed in ms.

Sensitive nerve conduction velocity (SNCV) was also recorded. The tail skin electrodes were placed as follows: a reference needle inserted at the base of the tail and an anode needle placed 30 mm away from the reference needle toward the extremity of the tail. A ground needle electrode was inserted between the anode and reference needles. The caudal nerve was stimulated with a series of 20 pulses (for 0.2 ms) at an intensity of 12.8 mA. The velocity was expressed in m/s.

H-wave reflex was recorded in the hind footpad muscle after stimulation of the sciatic nerve. A reference electrode and a ground needle were placed on the lower back of the rat. The sciatic nerve was stimulated with a single 0.2 ms pulse at supramaximal intensity. The amplitude (mV) of H wave and the proportion of animal lacking H wave response were the parameters studied.

Example 18

Morphometric Analysis

With vincristine, morphometric analysis was performed 2 week after the end of vincristine administration on 3 animals per group. The animals were anesthetized by IP injection of 100 mg/kg Imalgène 500®. A 5 mm segment of sciatic nerve was excised, fixed overnight with 4% glutaraldehyde (Sigma, L'Isle d'Abeau-Chesnes, France) in phosphate buffered saline (PBS) (pH=7.4) and maintained in 30% sucrose and stored at 4° C. until further processing. At the time of use, the nerve sample was post-fixed in 1% osmium tetroxide (Sigma, L'Isle d'Abeau-Chesnes, France) in PBS for 2 h, dehydrated in serial alcohol solution, and embedded in Epon. Embedded tissues were then placed at 70° C. during 3 days to allow polymerization of the tissue wax. Cross sections of 1.5 μm thick were performed and they were stained with a 1% toluidine blue solution (Sigma, L'Isle d'Abeau-Chesnes, France) for 2 min, dehydrated and mounted on Eukitt. Twelve sections per sample were examined using an optical microscope (Nikon, Tokyo, Japan) and analyzed using, a semi-automated digital image analysis software (Biocom, France). The fiber diameter (a), axon diameter (b), and myelin thickness (c) were measured as illustrated below.

For cisplatin treatment in Example 8, morphometric analysis was performed at the end of the experiment (week 6) on 3 animals per group. The total number of fibers per nerve section was obtained from 3 randomized slices of each sample. The counting was performed on 2 selected fields per slice.

For cisplatin in Example 13, morphometric analysis was performed at days 23 and 44 on 3 animals per group. The number of degenerated and non-degenerated fibers on the entire surface of each nerve section was counted by an operator in a blinded fashion. All the results (except the data expressed as ratio value) were reported as percentage of changes in reference to the control value.

Example 19

Data Analysis

All data are reported as mean values±SEM. Statistical analyses were performed using Statview for windows (SAS Institute Inc.). Comparisons of data from two treatment groups (control vs. vehicle) were performed by using unpaired student t-test. Data from more than two treatment groups were analyzed by Anova, followed by Dunnett's test for multiple comparisons test. Data were compared over the time course of the experiment by Manova, which allows multiple analysis of variance of several groups with time (i.e., longitudinal analysis of data) and Dunnett's test was used to detect which groups differ from which other groups. Individual time points of interest were analyzed further by using Anova. For the statistical analysis of data showing the proportion of animal presenting H-wave signal, 0 was assigned to animal demonstrating H-wave and 1 was assigned to animal lacking H-wave. For such a nominal data, $\chi^2$-test was used to perform the statistical analysis. Statistical analyses revealing p values less or equal to 0.05 were deemed significant.

To simplify the reading of graphs, only the statistical results for each time points after Anova analysis followed by Dunnett's test were shown. Manova analysis followed by Dunnett's test which compares the entire data over the time were only mentioned in the text.

Example 20

Effect of IL-6 in the Anti-Tumor Activity of Various Chemotherapy Drugs In Vitro In Examples 1-14 it was shown that IL-6 treatment could prevent and delayed neuropathy in rat intoxicated with either vincristine, cisplatin and taxol treatment. However, it is important to demonstrate that the activity of IL-6 in inhibition of neuropathy by chemotherapeutic agents does not involve impairing chemotherapeutic properties of the agents related to killing malignant cells.

To address this issue, the effects of IL-6 on the anti-tumor activity of various anti-tumor drugs such as vincristine, cisplatin, carboplatin, taxol or the combination carboplatin-taxol were investigated in vitro using cultures of two tumor cell lines, human lung (SK-MES1) and breast (MCF7) tumor cell lines.

The human lung (SK-MES1) and breast (MCF7) tumor cell lines were obtained from ATCC. The cell lines were maintained in Dulbecco's MEM medium (Gibco; Invitrogen, Cergy-Pontoise, France, ref. 41965039) supplemented with 1% antibiotic/antimicotic mixture solution (Gibco, ref. 15240062), and 10% heat-inactivated foetal bovine serum (Gibco, ref. F7524, batch 92K3387). The cells were amplified in Nunc tissue culture flasks (80 cm2) in a humidified incubator at 37° C. with 5% CO2 in 95% air. Cultures were sub-cultured twice a week.

The effects of IL-6 on the anti-proliferative effects of vincristine, cisplatin, carboplatin and taxol were evaluated using the acid phosphatase activity assay as described in Example 22. The enzymatic activity has been proven to be proportional to the number of living cells (Ueda et al.; 1994).

Three days after the last replication, tumor cells were seeded in 96 well-plates (TPP, VWR International, Fontenay-sous-bois, France) at a density of 1,500 cells (MCF7 line) or 3,000 cells (SK-MES1 line) per well, in a total volume of 100 µl/well and incubated overnight in a humidified incubator at 37° C. with 5% CO2 in 95% air. Cell cultures were then intoxicated by addition of vincristine (10 nM), cisplatin (2.5 mM), carboplatin (25 mM), taxol (30 nM for MCF7 cells and 50 nM for SK-MES1 cells) or a mixture of carboplatin (10 mM) and taxol (10 nM) into the cell culture medium. IL-6 (in buffer solution at 1.8 mg/ml, PH: 7) was immediately added at concentrations of 0, 3, 12, 50 or 200 ng/ml.

Four days after the initiation of the intoxication, acid phosphatase activity (Example 21) in each cell culture was assessed.

The results showed that in both of the tumor cell lines, vincristine (10 mM), cisplatin (2.5 µM), and carboplatin (25 µM) induced a significant decrease (about 50%) in cell survival as compared to control non-treated cell cultures ($p \leq 0.001$, Fisher's test) (FIG. 30 A, B, C, D, I, J respectively). In the presence of IL-6, the survival of vincristine or cisplatine or carboplatin treated MCF7 cells did not change significantly ($p > 0.05$, One-way Anova) the survival of vincristine-cisplatin or carboplatin intoxicated cells (FIG. 30 A, C, I respectively). In the presence of IL-6, the survival of vincristine or cisplatine treated SK-MES1 cells did not change significantly ($p > 0.05$, One-way Anova) (FIG. 30 B, D). In contrast, carboplatin-intoxicated SK-MES1 cells showed a significant ($p \leq 0.05$, One-way Anova) decrease of survival in the presence of IL-6 (FIG. 30 J).

Taxol (30 nM) induced about 55% decrease in the survival of MCF7 cell line ($p \leq 0.001$, Fisher's test) (FIG. 30 E). The cytotoxicity of this concentration of taxol appeared slightly enhanced in SK-MES1 cells, showing about 70% decrease of survival (FIG. 30 F). In both, MCF7 or SK-MES1 cells, treatment with IL-6 did not change the effect of taxol on the cell survival ($p > 0.05$, One-way Anova) (FIGS. 30 E and F respectively).

With the combination of 10 µM carboplatin and 10 nM taxol, 40% of decrease in survival of both types of tumor cell lines was observed ($p \leq 0.001$, Fisher's test) (FIGS. 30 G and H). The survival of both types of tumor cell lines intoxicated with the combination of carboplatin and taxol remained unchanged ($p > 0.05$, One-way Anova) in the presence of IL-6.

In the above experiments, the potential drug interaction between IL-6 and various chemotherapeutic agents in vitro was assessed. The in vitro results showed that IL-6 did not impair the anti-tumor activity of various chemotherapy agents tested.

Example 21

Effect of IL-6 in the Anti-Tumor Activity of Cisplatin In Vivo

The following experiment was carried out to check potential drug interaction between IL-6 and the chemotherapeutic agent in vivo. For that purpose, the effect of IL-6, alone and/or in combination with cisplatin, on human WiDr colon carcinoma growth in nude mice was evaluated.

Balb/c nude mice are used since have proven to be susceptible host systems for the growth of human WiDr colon carcinoma tumor cells. WiDr cells were provided by the bank of the National Cancer Research Institute Genova-Italy. Cell species: human 78-year-old female, tissue: colon, tumor: colon adenocarcinoma, accession number: ICLC HTL00003.

The WiDr cells were cultured in medium, DMEM+2 mM glutamine+10% FBS in continuous culture and grown as monolayer, epithelial morphology.

64 female Balb/c nude mice were purchased from Charles River Italia S.p.A., Via Indipendenza 11-22050 CALCO (Lecco). During the pre-treatment acclimatization period the animals were clinically observed every day.

Animals were housed in a ventilated laminar flow cabinet with temperature and relative humidity of 28° C.±2 and 55%±10, respectively. There were approximately 15-20 air changes per hour. The room was illuminated by artificial lighting with a 12-hour circadian cycle (7 a.m.-7 p.m.).

No more than 3 mice were housed in each cage. Each cage bore a label containing the experiment number, the group, the animal number, the date of experiment initiation and that of inoculation. Cages and bedding were changed twice a week. Cages, sawdust bedding and drinking bottles were sterilized in an autoclave before each cage change.

Body weight was recorded twice a week for 4 weeks following cell injection.

Tumor size was recorded twice a week for 4 weeks starting 4 days after cell inoculation.

At the end of a 4-week observation period, the animals were sacrificed by an i.p. injection of an overdose of sodium thiopentale.

Each Balb/c nude mice (about 20-25 g body weight) was inoculated subcutaneously (s.c.) with $10^7 + 5\%$ WiDr cells/mouse (0.2 mL/mouse of cell suspension) on day 1.

The animals were then randomly allocated to the following experimental groups of 8 rats per group:

A group administered with 0.02% mouse albumin (Sigma) in 40 mM phosphate buffer at pH=7.0, s.c., a group administered with 3.5 mg/kg Cis-platinum, i.p. (in 0.9% NaCl sterile solution for injection), three groups of rats each treated with IL-6 (in 0.02% mouse albumin in 40 mM phosphate buffer at pH=7.0), s.c. at 3, 10 or 30 µg/kg and three groups of rats treated with IL-6 either at 3, 10 or 30 µg/kg IL-6, s.c. in combination with cis-platinum 3.5 mg/kg, i.p.

IL-6 at 3, 10 and 30 mg/kg was given s.c. daily (10 mL/kg) from day 4 up to day 18. Cisplatinum (Sigma) 3.5 mg/kg (10 mL/kg) i.p. was given only 4, 8, 12 and 18 days following cell injection. Tumor size was recorded twice a week for 4 weeks starting 4 days after cell inoculation. Tumor volume (in mm$^3$) was estimated according to the formula (Geran R. I. et al., Cancer Chemotherapy Reports (1972) Part 3, 3(2): 51): Tumor volume (in mm$^3$)=(longer diameter)×(shorter diameter)$^2$/2.

The results obtained show that cisplatin administered at 3.5 mg/kg on days 4, 8, 12 and 18 was able to reduce tumor growth and the anti-proliferative effect (FIG. 31). The effect of cisplatin was maintained after cisplatin interruption. Significant tumor inhibitions were achieved on days 18 ($p < 0.05$), 22 ($p < 0.01$) and 25 ($p < 0.001$; one-way ANOVA followed by Tukey test.

IL-6 administration alone, at the doses of 3, 10 and 30 µg/kg administered daily by subcutaneous route from day 4 up to day 18, did not significantly affect the growth of the tumor (FIG. 32). The combination of IL-6 with cisplatin resulted in similar inhibitory tumor growth as the treatment of cisplatin alone (FIG. 33).

In conclusion, IL-6, alone or in combination with cis-platinum, did not interfere with either WiDr cell tumor growth or the chemotherapeutic action of cis-platinum.

Example 22

Phosphatase Assay

After removal of the culture medium, cells were rinsed with phosphate-buffered saline (PBS, Gibco, ref. 14190-094) and further incubated for 90 min at 37° C. in 100 µl of buffer containing 0.1 mol/l sodium acetate (pH 5.5), 0.1% Triton X100 (Sigma, ref. T9284) and 10 mmol/l p-nitrophenyl phosphate (Sigma, ref. N9389). Reaction was stopped by addition of 10 µl of 1 mol/l sodium hydroxide aqueous solution (Laboratoire de Produit Chimiques de la Robertsau, Strasbourg, France; ref. 28.252.293). Absorbance of the colored solution was measured at 405 nm in a microplate reader (Labsystems Multiskan Bichromatic, EST-LAB, Strasbourg, France).

The results were expressed as percentage of optical density of the control cell cultures. The heights of the columns represent mean±SEM of percentages of 5-6 wells from two independent cultures.

A global analysis of the data was done using a one way analysis of variance (Anova). Where applicable, Fisher's PLSD test was used for multiple pairwise comparison. The level of significance was set at $p \leq 0.05$.

Example 23

Recombinant Human IL-6 Production

Recombinant human IL-6 (r-hIL-6) is produced in genetically engineered Chinese Hamster Ovary (CHO) cells. The production process begins with the growth and expansion of cells from a working cell bank (WCB) and continues under conditions where r-hIL-6 is secreted into the culture medium. The r-hIL-6 was harvested and purified from culture medium of the engineered cells. Purity was above 99.6% and potency $23.3 \times 10^6$ IU/ml (based on a Hybridoma growth factor (HGF) activity of IL-6 of Van Damme J, Van Snick J. Dev Biol Stand. 1988; 69:31-8).

The invention claimed is:

1. A method for treating and/or reducing chemotherapy-induced peripheral neuropathy, comprising administering an effective dose of IL-6 in a range of 0.06 to 3 µg/kg body weight, or a fused protein comprising IL-6 and an immunoglobulin or IL-6 and a constant region of a immunoglobulin, or a salt thereof, to a patient undergoing treatment with at least one chemotherapeutic agent or to a patient in which at least one chemotherapeutic agent is being co-administered, so as to treat and/or reduce chemotherapy-induced peripheral neuropathy.

2. The method according to claim 1, wherein the patient is a high-risk patient who suffers from chemotherapy-induced peripheral neuropathy.

3. The method according to claim 1, wherein the patient exhibits high levels of IL-6 receptor in the circulation.

4. The method according to claim 1, wherein the IL-6, or a fused protein comprising IL-6 and an immunoglobulin or IL-6 and a constant region of a immunoglobulin, or a salt thereof, is administered daily.

5. The method according to claim 1, wherein the IL-6, or a fused protein comprising IL-6 and an immunoglobulin or IL-6 and a constant region of a immunoglobulin, or a salt thereof, is administered three times per week.

6. The method according to claim 1, wherein the IL-6, or a fused protein comprising IL-6 and an immunoglobulin or IL-6 and a constant region of a immunoglobulin, or a salt thereof, is administered daily or three times per week for at least two weeks.

7. The method according to claim 1, wherein the IL-6, or a fused protein comprising IL-6 and an immunoglobulin or IL-6 and a constant region of a immunoglobulin, or a salt thereof, is administered subcutaneously.

8. The method of claim 1, wherein said at least one chemotherapeutic agent is vincristine.

9. The method of claim 1, wherein said at least one chemotherapeutic agent is cisplatin.

10. The method of claim 1, wherein said at least one chemotherapeutic agent is taxol.

* * * * *